United States Patent
Yates et al.

(10) Patent No.: US 10,314,645 B2
(45) Date of Patent: Jun. 11, 2019

(54) SURGICAL END EFFECTORS WITH INCREASED STIFFNESS

(71) Applicant: Ethicon Endo-Surgery, LLC, Guaynabo, PR (US)

(72) Inventors: David C. Yates, West Chester, OH (US); Rudolph H. Nobis, Mason, OH (US); Barry C. Worrell, Centerville, OH (US)

(73) Assignee: Ethicon LLC, Guaynabo, PR (US)

( * ) Notice: Subject to any disclaimer, the term of this patent is extended or adjusted under 35 U.S.C. 154(b) by 366 days.

(21) Appl. No.: 15/071,607

(22) Filed: Mar. 16, 2016

(65) Prior Publication Data
US 2017/0265933 A1  Sep. 21, 2017

(51) Int. Cl.
*A61B 17/29* (2006.01)
*A61B 18/14* (2006.01)
*A61B 17/295* (2006.01)

(52) U.S. Cl.
CPC .......... *A61B 18/1445* (2013.01); *A61B 17/29* (2013.01); *A61B 17/295* (2013.01); *A61B 18/1442* (2013.01); *A61B 2017/2926* (2013.01); *A61B 2018/1452* (2013.01); *A61B 2018/1455* (2013.01)

(58) Field of Classification Search
CPC . A61B 18/14; A61B 18/1442; A61B 18/1445; A61B 18/1447; A61B 2018/00589; A61B 2018/00595; A61B 2018/00601; A61B 2018/00607; A61B 2018/1452; A61B 2018/1455; A61B 17/29; A61B 17/295; A61B 2017/2902; A61B 2017/2926; A61B 2017/2932; A61B 2017/2939; A61B 2017/294; A61B 2017/2944; A61B 2017/2945; A61B 34/70
See application file for complete search history.

(56) References Cited

U.S. PATENT DOCUMENTS

| | | | | |
|---|---|---|---|---|
| 6,083,223 | A * | 7/2000 | Baker | A61B 18/1445 606/49 |
| 6,113,598 | A * | 9/2000 | Baker | A61B 18/1445 606/38 |
| 6,500,176 | B1 | 12/2002 | Truckai et al. | |
| 6,533,784 | B2 | 3/2003 | Truckai et al. | |
| 6,656,177 | B2 | 12/2003 | Truckai et al. | |

(Continued)

*Primary Examiner* — Daniel W Fowler
*Assistant Examiner* — Bradford C. Blaise
(74) *Attorney, Agent, or Firm* — Mintz Levin Cohn Ferris Glovsky and Popeo, P.C.

(57) ABSTRACT

Surgical end effectors with increased stiffness are described herein. Increased stiffness can be accomplished in a variety of manners, including by increasing a height of each jaw member of an end effector. For example, end effector jaw members can include tapered heights that decrease from a proximal end of the jaw member to a distal end thereof. In one embodiment, first and second jaw members can each have a height measured at a proximal end thereof that is greater than half of an overall height of the end effector, while at a distal end thereof a sum of heights of the first and second jaw members can approximately equal the overall height of the end effector. Overlapping or otherwise fitting such jaw members together can create an end effector with greater stiffness that can be used to apply greater compression force to tissue during operation.

19 Claims, 26 Drawing Sheets

(56) References Cited

U.S. PATENT DOCUMENTS

| | | |
|---|---|---|
| 6,770,072 B1 | 8/2004 | Truckai et al. |
| 6,802,843 B2 | 10/2004 | Truckai et al. |
| 6,887,240 B1 * | 5/2005 | Lands ............... A61B 17/29 |
| | | 606/207 |
| 6,905,497 B2 | 6/2005 | Truckai et al. |
| 6,913,579 B2 | 7/2005 | Truckai et al. |
| 6,926,716 B2 | 8/2005 | Baker et al. |
| 6,929,622 B2 | 8/2005 | Chian |
| 6,929,644 B2 | 8/2005 | Truckai et al. |
| 7,011,657 B2 | 3/2006 | Truckai et al. |
| 7,041,102 B2 | 5/2006 | Truckai et al. |
| 7,070,597 B2 | 7/2006 | Truckai et al. |
| 7,083,619 B2 | 8/2006 | Truckai et al. |
| 7,087,054 B2 | 8/2006 | Truckai et al. |
| 7,112,201 B2 | 9/2006 | Truckai et al. |
| 7,125,409 B2 | 10/2006 | Truckai et al. |
| 7,169,147 B2 | 1/2007 | Nosel |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,311,709 B2 | 12/2007 | Truckai et al. |
| 7,354,400 B2 | 4/2008 | Asafusa et al. |
| 7,381,209 B2 | 6/2008 | Truckai et al. |
| 8,128,649 B2 * | 3/2012 | Slater ............. A61B 17/3201 |
| | | 606/205 |
| 9,161,803 B2 | 10/2015 | Yates et al. |
| 2009/0076506 A1 | 3/2009 | Baker |
| 2010/0036370 A1 | 2/2010 | Mirel et al. |
| 2011/0060334 A1 * | 3/2011 | Brandt ............ A61B 18/1445 |
| | | 606/48 |
| 2011/0251606 A1 * | 10/2011 | Kerr ............... A61B 18/1402 |
| | | 606/34 |
| 2011/0301599 A1 * | 12/2011 | Roy ............... A61B 18/1445 |
| | | 606/46 |
| 2013/0035687 A1 * | 2/2013 | Hiller ............. A61B 18/1445 |
| | | 606/45 |
| 2013/0066318 A1 * | 3/2013 | Kerr ................. A61B 17/29 |
| | | 606/52 |
| 2013/0296848 A1 * | 11/2013 | Allen, IV ........ A61B 18/1445 |
| | | 606/41 |
| 2013/0345706 A1 * | 12/2013 | Garrison .......... A61B 18/1447 |
| | | 606/51 |
| 2014/0005653 A1 | 1/2014 | Shelton, IV et al. |
| 2014/0214019 A1 | 7/2014 | Baxter, III et al. |
| 2014/0276719 A1 | 9/2014 | Parihar |
| 2014/0378971 A1 * | 12/2014 | Yamada .......... A61B 17/2202 |
| | | 606/51 |
| 2015/0025528 A1 * | 1/2015 | Arts ............... A61B 18/1445 |
| | | 606/37 |
| 2015/0289767 A1 * | 10/2015 | Keller ................. A61B 18/18 |
| | | 600/549 |

* cited by examiner

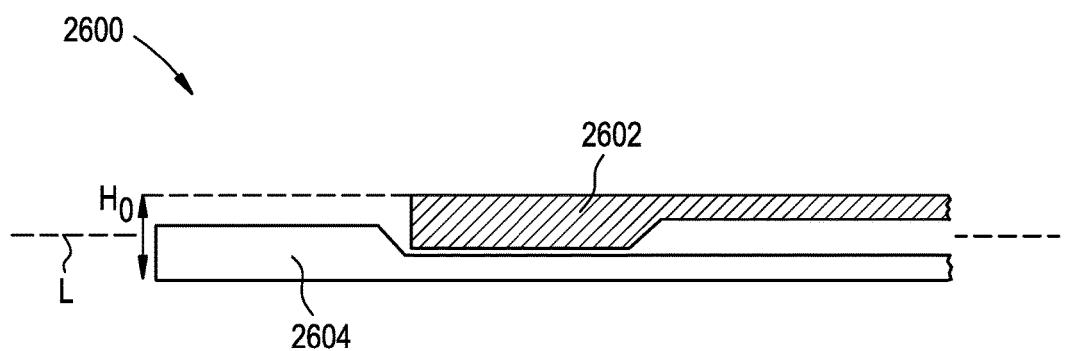
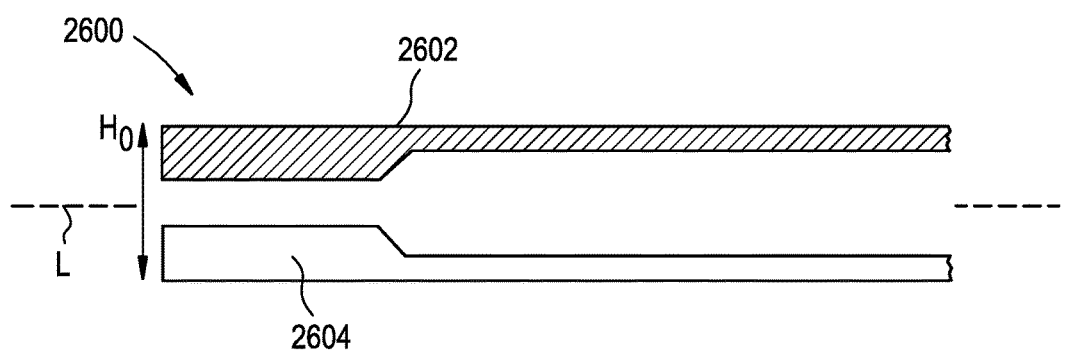

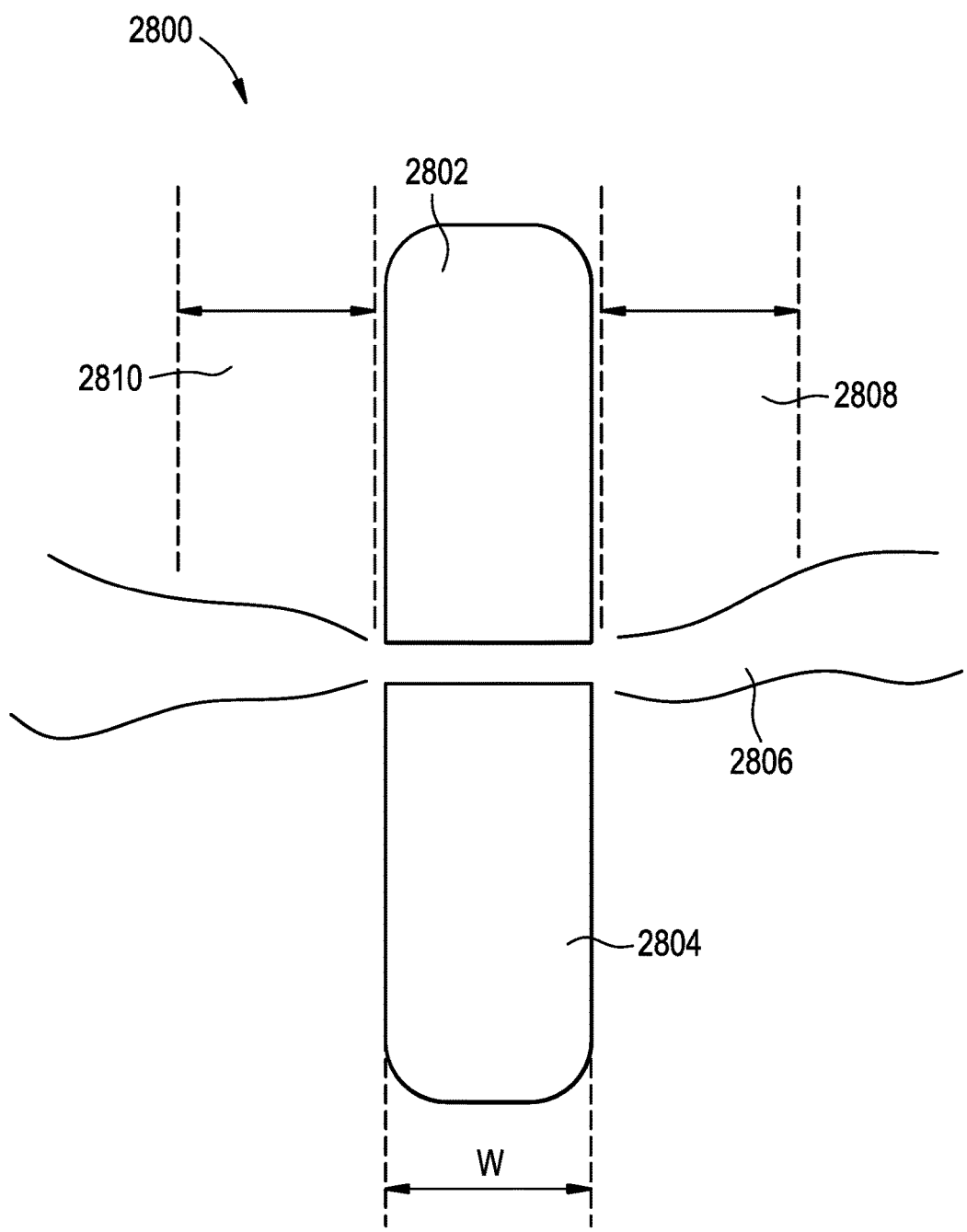

SURGICAL END EFFECTORS WITH INCREASED STIFFNESS

FIELD

This disclosure relates generally to surgical instruments and, more particularly, to surgical end effectors used to treat tissue.

BACKGROUND

Surgical devices are used in various open, endoscopic, and laparoscopic surgeries to manipulate tissue, seal or staple tissue, and/or transect tissue volumes and blood vessels. These devices can include end effectors having opposed jaw members that move relative to one another to grasp tissue therebetween. Certain of these devices also include a cutting mechanism that can be advanced through the grasped tissue to transect it. In some cases, the cutting mechanism can be designed to travel within a track formed in one or both jaw members of the cutting mechanism. Moreover, as the cutting mechanism is advanced along a length of the jaw members, it can apply a compressive force to at least one of the jaw members. This compressive force can be combined with delivery of energy to seal tissue volumes and blood vessels being transected. For example, electrical energy can be applied to the grasped tissue to seal it before tissue transection is completed. Such energy can be delivered by various mono-polar and bi-polar radio frequency (RF) electrodes or other energy delivery structures coupled to the jaw members.

Prior art surgical end effectors often are constructed with opposed, generally symmetrical jaw members. The jaw members may be pivotably coupled to one another and may be configured such that they both move or such that one jaw member moves relative to a stationary jaw member. Each generally symmetrical jaw member can have approximately equal widths and heights to the other, and the widths can be greater than the heights to maximize the size of electrode that can be coupled to the surface of each jaw member on either side of the transecting cutting mechanism path.

One problem associated with prior art end effector design is a lack of sufficient stiffness that can be required or desirable in certain situations. For example, in some cases it can be desirable to seal tissue using electrical or other energy without transecting the tissue using the cutting mechanism. In such a situation, it can be difficult to achieve sufficient tissue compression to create a good seal using only the force provided by a jaw closure mechanism. This is typically not a concern when transecting tissue, as the cutting mechanism can be configured to apply a compressive force to the tissue as it advances down the track formed in the jaw members. Applying energy to the tissue concurrently with this increased compression force can ensure sealing of the tissue.

The inability of a jaw closure mechanism to apply sufficient compression forces to tissue is largely due to insufficient stiffness in the jaw members themselves. In particular, closure mechanisms typically apply force to a proximal end of the jaw members to urge them toward one another, thereby compressing tissue between the jaw members. The jaw members, however, deflect along their lengths moving toward a distal end thereof. As a result, insufficient compressive force may be found at the distal end of the end effector and possibly also closer to the proximal end thereof.

Moreover, when dealing with surgical instruments there is often a need to maximize strength while minimizing size. This can be particularly true for minimally invasive procedures or other operations where access to a surgical site is limited to an opening of a certain size, diameter, etc. As noted above, prior art surgical end effectors are often relatively wide compared to their height in order to maximize the size of any electrode or other energy delivery structure positioned on tissue-facing surfaces of the jaw members. This width can be problematic if the device is required to pass through, for example, a smaller diameter passageway.

Accordingly, there is a need for surgical instruments or devices having end effectors with increased stiffness that permit, for example, imparting greater compressive forces to tissue grasped by jaw members. There is also a need for surgical end effectors that maximize jaw member stiffness and surface area available for mounting electrodes or other energy delivery structures, while minimizing the size of the end effector to facilitate introduction in minimally invasive and other surgical procedures.

SUMMARY

The present disclosure generally provides devices and methods for increasing the stiffness of surgical end effector jaw members such that sufficient compressive forces can be applied to tissue using a closure mechanism that acts on a proximal end of the end effector. Minimizing any flexing in the jaw members along their length can more effectively transmit force applied by a closure mechanism to tissue disposed between the jaw members. Imparting greater compressive forces to tissue can increase the quality of a tissue weld or seal created by delivering energy to the tissue, and can permit sealing tissue without transection in some cases. Increased stiffness can be accomplished, for example, by increasing a height (measured in the plane defined by the movement of the jaw members) of one or more of the end effector jaw members such that the jaw member possesses an increased area moment of inertia to resist flexing or other deformation. Moreover, in some embodiments the height of one or more of the end effector jaw members can be increased without increasing an overall height of the end effector. This can be accomplished, for example, by providing sidewalls on one jaw member and nesting the other jaw member within a cavity defined by the sidewalls.

In addition, the devices and methods described herein can maximize a surface area of tissue contacting surfaces of end effector jaw members while minimizing the overall height and width of the end effector. This can allow for the use of larger electrodes or other energy delivery structures without requiring a larger end effector. In some embodiments, the surface area of tissue contacting surfaces can be increased by orienting the tissue-contacting surfaces transversely with respect to a typical neutral plane defined by end effector jaw members. Orienting tissue contacting surfaces in this manner can span a diagonal dimension of the end effector, thereby increasing available surface area for energy delivery. Still further, in some embodiments the tissue contacting surfaces can be curved as opposed to planar, a modification that can also increase available surface area for delivering energy to tissue.

In one aspect, a surgical end effector is provided that includes first and second jaw members movable relative to one another between an open position and a closed position to clamp tissue therebetween. The first and second jaw members can each have a height measured at a proximal end thereof that is greater than half of an overall height of the end effector. Further, a sum of heights of the first and second jaw members measured at a distal end thereof can be approximately equal to the overall height of the end effector. Height can be measured along an axis that is perpendicular to a longitudinal axis of the end effector and contained within a plane in which the first and second jaw members move relative to one another.

The devices and methods described herein can have a number of additional features and/or variations, all of which are within the scope of the present disclosure. In some embodiments, for example, the height of each of the first and second jaw members can taper from a proximal end to a distal end thereof. In other embodiments, the height can decrease in discrete steps from a proximal end to a distal end of the jaw members.

In other embodiments, the end effector can further include an actuator coupled to at least one of the first and second jaw members and configured to move it relative to the other jaw member. As such, the actuator can function as the closure mechanism referenced above. In some embodiments, the actuator can be pivotably coupled to the at least one of the first and second jaw members and configured to translate along the longitudinal axis of the end effector. In some embodiments, for example, the first jaw member can be pivotably coupled to the actuator and also pivotably coupled to the second jaw member. As a result, translating motion of the actuator can result in pivoting motion of the first jaw member relative to the second jaw member, thereby moving the jaw members between an open position and a closed position to clamp tissue therebetween.

In order to maximize the amount of compressive force that can be applied to the tissue disposed between the first and second jaw members when in the closed position, the actuator can be configured in some embodiments to contact the at least one of the first and second jaw members with a planar distal-facing surface when the first and second jaw members are in the closed position. Such an interface provides a larger surface area to apply force to at least one of the jaw members when in the closed position.

In still other embodiments, each of the first and second jaw members can include a tissue contacting surface configured to abut against tissue clamped between the first and second jaw members when in the closed position, and an electrode can be disposed on the tissue contacting surface of at least one of the first and second jaw members.

One manner of increasing a height of a jaw member is to provide sidewalls that protrude above, for example, a tissue contacting surface. Accordingly, in some embodiments at least one of the first and second jaw members can include sidewalls that extend from the tissue contacting surface such that tissue is stretched between the sidewalls as the first and second jaw members move from the open position to the closed position. This can provide the added benefit of tensioning tissue as it is clamped between the first and second jaw members, which can reduce the amount of force necessary to transect the tissue with, for example, a cutting mechanism.

As noted above, in some embodiments the end effector can further include a cutting mechanism configured to transect tissue clamped between the first and second jaw members. In such embodiments, each of the first and second jaw members can include a slot formed along a length thereof that is configured to receive a cutting element configured to cut tissue clamped between the first and second jaw members. In certain embodiments, the cutting element can be further configured to apply an additional compressive force to the tissue clamped between the first and second jaw members as the cutting element is advanced distally along the slot or track formed in the first and second jaw members.

The height dimensions described above can, in some embodiments, be overall heights of the various components of the end effector. In other embodiments, the referenced heights can be heights as measured at specific places along a width axis of the end effector. For example, in some embodiments the height of the first jaw member can be measured along a central portion thereof, and the height of the second jaw member can be measured along a peripheral portion thereof. The central portion can include, for example, the portion of the first jaw member positioned at or near to a central longitudinal axis of the end effector and/or first jaw member, while the peripheral portion can include, for example, an outer edge of the second jaw member or portion adjacent thereto.

In another aspect, a surgical end effector is provided that includes a first jaw member having sidewalls defining a central recess, wherein a height of the sidewalls increases from a distal end to a proximal end of the first jaw member. The end effector can further include a second jaw member pivotably coupled to the first jaw member and including a central portion configured to be received within the central recess of the first jaw member. Moreover, a height of the central portion can increase from a distal end to a proximal end of the second jaw member.

As with the instrument described above, a number of variations and additional features are possible. For example, in some embodiments the height of the sidewalls of the first jaw member at the proximal end thereof and the height of the central portion of the second jaw member at the proximal end thereof can each be greater than half of an overall height of the end effector at a proximal end thereof.

In other embodiments, the height of the sidewalls of the first jaw member and the height of the central portion of the second jaw member can increase linearly from a distal end thereof to a proximal end thereof. In still other embodiments, the first jaw member can include a first tissue contacting surface extending between the sidewalls and forming a bottom of the central recess, and the second jaw member can include a second tissue contacting surface disposed on the central portion and configured to oppose the first tissue contacting surface.

In another aspect, a surgical end effector is provided that includes a first jaw member and a second jaw member that is coupled to and movable relative to the first jaw member to clamp tissue therebetween. Moreover, one of the first and second jaw members can be configured to provide greater stiffness relative to the other jaw member.

As with the instrument described above, a number of variations and additional features are possible. For example, in some embodiments a height of at least one of the first jaw member and the second jaw member can be greater than a width thereof. Height can be measured along a first axis that is perpendicular to a longitudinal axis of the end effector and contained within a plane in which the first and second jaw members move relative to one another. Width can be measured along a second axis that is perpendicular to both the longitudinal axis of the end effector and the first axis.

In other embodiments, a height of at least one of the first jaw member and the second jaw member can taper from a proximal end to a distal end thereof. In still other embodiments, the height can decrease in discrete steps from a proximal end to a distal end of the jaw members.

In certain embodiments, the first jaw member and the second jaw member can both include a tissue contacting surface configured to abut against tissue clamped between the first and second jaw members. Moreover, at least one of the first jaw member and the second jaw member can include sidewalls that extend from the tissue contacting surface such that tissue is stretched between the sidewalls as it is clamped between the first jaw member and the second jaw member.

In another aspect, a surgical end effector is provided that includes first and second jaw members movable relative to one another between an open position and a closed position to clamp tissue therebetween, as well as an electrode disposed on a surface of at least one of the first and second jaw members. The electrode can be configured to contact tissue clamped between the first and second jaw members when in the closed position. Further, a height of each of the first and second jaw members can be greater than a width thereof, and the height can be measured along a first axis that is perpendicular to a longitudinal axis of the end effector and contained within a plane in which the first and second jaw members move relative to one another. Width can be measured along a second axis that is perpendicular to both the longitudinal axis of the end effector and the first axis. Further, the surface of at least one of the first and second jaw members can be transverse to the second axis.

A number of variations are possible here as well. For example, in some embodiments the surface can be planar, while in other embodiments the surface can be curved. In some embodiments, the surface can extend between diagonally opposed corners of the end effector when viewing a plane defined by the first axis and the second axis. In still other embodiments, the first jaw member can include the surface and the second jaw member can include a complementary surface facing the surface. In some embodiments, the complementary surface of the second jaw member can also include an electrode disposed thereon.

In other embodiments, the first and second jaw members can be further configured to move relative to one another between an insertion configuration, in which a distal end of the first jaw member is positioned proximal to a proximal end of the second jaw member, and a deployed configuration, in which the first and second jaw members are aligned along the longitudinal axis of the end effector. And in some embodiments, the first and second jaw members can be further configured to overlap with one another along the first axis when in the insertion configuration so as to reduce an overall height of the end effector.

Any of the features or variations described above can be applied to any particular aspect or embodiment of the disclosure in a number of different combinations. The absence of explicit recitation of any particular combination is due solely to the avoidance of repetition in this summary.

BRIEF DESCRIPTION OF THE DRAWINGS

FIG. 26 is a schematic side view illustration of one embodiment of end effector jaw members arranged in an insertion configuration;

FIG. 27 is a schematic side view illustration of the end effector jaw members of FIG. 26 in a deployed configuration; and FIG. 28 is a schematic front view illustration of one embodiment of end effector jaw members and adjacent thermal zones of elevated temperature due to energy delivery to tissue clamped between the jaw members.

DETAILED DESCRIPTION

Figure 1:
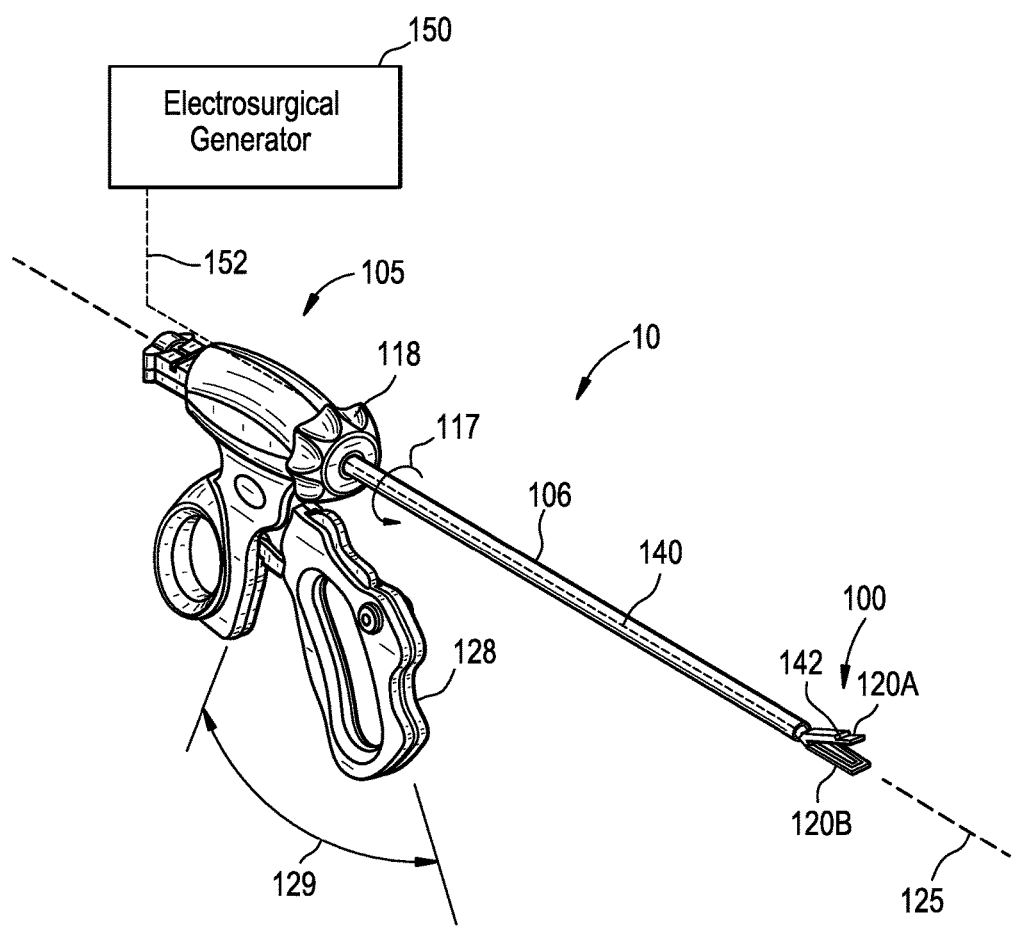
FIG. 1 is a perspective view illustration of a prior art surgical instrument including an end effector for grasping, sealing, and transecting tissue.

Certain exemplary embodiments will now be described to provide an overall understanding of the principles of the structure, function, manufacture, and use of the devices and methods disclosed herein. One or more examples of these embodiments are illustrated in the accompanying drawings.

Those skilled in the art will understand that the devices and methods specifically described herein and illustrated in the accompanying drawings are non-limiting exemplary embodiments and that the scope of the present disclosure is defined solely by the claims. The features illustrated or described in connection with one exemplary embodiment may be combined with the features of other embodiments. Such modifications and variations are intended to be included within the scope of the present application. To the extent features are described herein as being a "first feature" or a "second feature," such numerical ordering is generally arbitrary, and thus such numbering can be interchangeable.

Additionally, to the extent that linear or circular dimensions are used in the description of the disclosed devices and methods, such dimensions are not intended to limit the types of shapes that can be used in conjunction with such devices and methods. A person skilled in the art will recognize that an equivalent to such linear and circular dimensions can easily be determined for any geometric shape. Still further, sizes and shapes of the devices, and the components thereof, can depend at least on the anatomy of the subject in which the devices will be used, the size and shape of components with which the devices will be used, and the methods and procedures in which the devices will be used.

Surgical devices and methods are described herein that provide for increasing the stiffness of surgical end effector jaw members such that increased compressive forces can be applied to tissue using a closure mechanism that acts on a proximal end of the end effector. Minimizing any flexing in the jaw members along their length can more effectively transmit force applied by a closure mechanism to tissue disposed between the jaw members. Imparting greater compressive forces to tissue can increase the quality of a tissue weld or seal created by delivering energy to the tissue, and can permit sealing tissue without transection in some cases. Increased stiffness can be accomplished, for example, by increasing a height (measured in the plane defined by the movement of the jaw members or the plane in which deflection occurs) of one or more of the end effector jaw members such that the jaw member possesses an increased area moment of inertia to resist flexing or other deformation. Moreover, in some embodiments the height of one or more of the end effector jaw members can be increased without increasing an overall height of the end effector. This can be accomplished, for example, by providing sidewalls on one jaw member and nesting the other jaw member within a cavity defined by the sidewalls.

In addition, the devices and methods described herein can maximize a surface area of tissue contacting surfaces of end effector jaw members while minimizing the overall height and width of the end effector. This can allow for the use of larger electrodes or other energy delivery structures without requiring a larger end effector. In some embodiments, the surface area of tissue contacting surfaces can be increased by orienting the tissue-contacting surfaces transversely with respect to a typical neutral plane defined by end effector jaw members. Orienting tissue contacting surfaces in this manner can result in the surfaces spanning a diagonal dimension of the end effector cross-section, thereby increasing available surface area for energy delivery. Still further, in some embodiments the tissue contacting surfaces can be curved as opposed to planar, a modification that can also increase available surface area for delivering energy to tissue.

FIG. 1 shows a prior art electrosurgical instrument 10. The electrosurgical instrument 10 can include a proximal handle end 105, a distal end effector 100, and an introducer or shaft member 106 disposed in-between. The end effector 100, shown in more detail in FIG. 2, can include a set of movable jaw members having a straight or curved shape and including a first, or upper, jaw member 120A and a second, or lower, jaw member 120B. The first jaw member 120A and the second jaw member 120B can each include an elongate channel 142 disposed along their respective middle portions. The first jaw member 120A and the second jaw member 120B can be coupled to an electrosurgical generator 150 through electrical leads in cable 152. The generator 150 can be used to selectively deliver electrical energy to tissue grasped between the first and second jaw members 120A, 120B. One example of an electrosurgical generator suitable for use with instruments of the type disclosed herein is the Gen11 generator from Ethicon Endo-Surgery, Inc., though other electrosurgical generators known in the art could also be utilized.

As seen in FIG. 1, the handle end 105 can include a lever arm 128 which can be pulled along a path 129. The lever arm 128 can be coupled to a translatable, reciprocating member 140 disposed within the introducer or shaft member 106. The handle can be any type of pistol-grip or other type of handle known in the art that is configured to carry actuator levers, triggers, or sliders for actuating the first jaw member 120A and the second jaw member 120B. The introducer or shaft member 106 can have a cylindrical, rectangular, or other cross-section and can include a thin-wall tubular sleeve that extends from the handle 105 to the end effector 100. The introducer or shaft member 106 can have a bore extending therethrough for carrying various actuator mechanisms for moving, e.g., the translatable, reciprocating member 140 or the first and second jaw members 120A, 120B, as well as electrical leads for delivery of electrical energy to electrosurgical components of the end effector 100.

The end effector 100 can be adapted for capturing, welding/sealing, and transecting tissue. The first jaw member 120A and the second jaw member 120B can close to thereby capture, clamp, or engage tissue between tissue facing or contacting surfaces thereof about a longitudinal axis 125 of the end effector. The first jaw member 120A and the second jaw member 120B can also apply compression to the tissue. The introducer or shaft member 106, along with the first jaw member 120A and the second jaw member 120B, can be rotated a full 360 degrees, as shown by arrow 117, relative to the handle 105 using, for example, a rotary controller 118. The first jaw member 120A and the second jaw member 120B can remain movable/operable while rotated to any angle.

Figure 3:
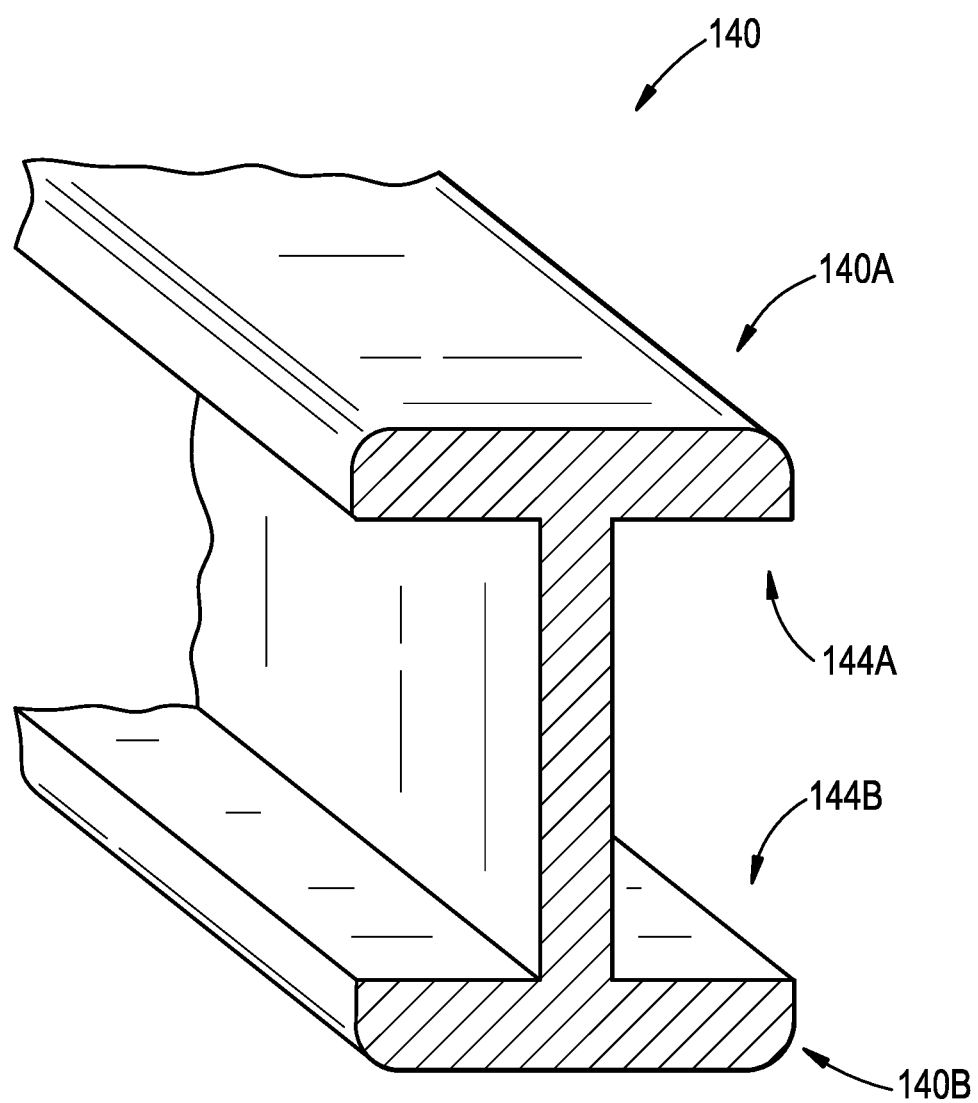
FIG. 3 is a detail view of a reciprocating member of the device of FIG. 1.

Channel 142 formed in the first jaw member 120A and second jaw member 120B can accommodate the movement of the reciprocating member 140, which may comprise a tissue-cutting element or mechanism, for example, a sharp distal edge. FIG. 3 shows a portion of a translatable, reciprocating member or reciprocating "I-beam" member 140. The lever arm 128 of handle 105 can be adapted to actuate the translatable member 140, which can also function as a jaw compression mechanism. For example, the translatable member 140 can be urged distally as the lever arm 128 is pulled proximally along the path 129. The distal end of the translatable member 140 can include a flanged "I"-beam configured to slide within channels 142 in the first and second jaw members 120A and 120B. The translatable member 140 can slide within the channels 142 and urge the first jaw member 120A toward the second jaw member 120B as it advances distally. The distal end of the translatable member 140 can include an upper flange 140A and a lower flange 140B. The flanges 140A and 140B can respectively define inner cam surfaces 144A and 144B for engaging outward facing surfaces of the first jaw member 120A and the second jaw member 120B, respectively. Urging the first jaw member 120A and the second jaw member 120B toward one another using the cam mechanisms of the reciprocating "I-beam" member 140 can apply compressive forces to tissue disposed therebetween. Various other cam mechanisms are known in the art and can also be employed.

The first jaw member 120A and the second jaw member 120B can each include tissue-gripping elements, such as teeth 143, disposed on the inner portions thereof. Furthermore, the first jaw member 120A can include one or more energy delivery surfaces 175A, and the second jaw member 120B can also include one or more energy delivery surfaces 175B. The energy delivery surfaces can extend in a "U" or other shape about the distal end of end effector 100. There can be intermediate members (e.g., lower intermediate member 185B) disposed between the energy delivery surfaces and the jaw members. The intermediate members can provide thermal and/or electrical insulation and can be formed from, for example, zirconia, partially stabilized zirconia, aluminum oxide, silicon nitride, alumina-chromia, hydroxyapatite, other non-conductive glass materials, other non-conductive ceramic materials, other non-conductive glass-ceramic materials, and high temperature tolerant polymers, such as nylon and others. In addition, if such materials are configured to contact tissue, they can be chosen based on various biocompatible properties suitable for the application.

The energy delivery surfaces 175A, 175B can be coupled to the electrosurgical generator 150 through electrical leads in cable 152 and can be configured to contact tissue and deliver electrosurgical energy to engaged tissue which is adapted to seal or weld the tissue. Moreover, the energy delivery surfaces 175A, 175B can be configured to operate in a monopolar configuration or a paired bi-polar configuration in which separate energy delivery surfaces (or portions thereof) operate with opposite polarities. The electrosurgical generator 150 can regulate the electrical energy delivered to the first and second energy-delivery surfaces 175A, 175B. The electrosurgical energy delivered by the generator 150 can include, for example, radiofrequency (RF) energy.

The above-described electrosurgical energy can be delivered through tissue captured or clamped between the jaw members 120A, 120B that is in contact with the first and second energy delivery surfaces 175A, 175B. Translatable member 140 can include an insulating layer in some embodiments to prevent member 140 from functioning as a conductive path for current delivery. Opposing first and second energy delivery surfaces can, in some embodiments, carry variably resistive positive temperature coefficient (PTC) bodies or matrices that are coupled to the electrosurgical generator 150 in series and parallel circuit components. In one embodiment, for example, the first energy delivery surface 175A and associated PTC body can have a first polarity (designated as "−") while the second energy delivery surface 175B and associated PTC body can have a second polarity (designated as "+"). PTC materials can "trip" and become more resistant once a selected trip current is exceeded. The first and second energy delivery surfaces can carry any of the PTC matrix and electrode components disclosed in U.S. Pat. No. 6,929,644, entitled "Electrosurgical Jaw Structure for Controlled Energy Delivery," and U.S. Pat. No. 6,770,072, entitled "Electrosurgical Jaw Structure for Controlled Energy Delivery," the entire disclosures of which are incorporated herein by reference. The use of PTC materials in electrosurgical instruments is also described in U.S. Pat. No. 7,112,201, entitled "Electrosurgical Jaw Structure for Controlled Energy Delivery," and U.S. Pat. No. 6,929,622, entitled "Electrosurgical Jaw Structure for Controlled Energy Delivery," the entire disclosures of which are incorporated herein by reference.

While the embodiment above describes a bipolar configuration of energy delivery structures disposed on jaw members of an end effector, other configurations are also possible. For example, one or more energy delivery structures can have a monopolar configuration in which electrosurgical energy can flow from the one or more energy delivery structures to a return pad located remotely therefrom.

A person skilled in the art will recognize other non-limiting examples of features that can be incorporated into the instrument 10 to assist in manipulating or otherwise operating the device. Examples can include: (1) an articulation lever for articulating the end effector 100; (2) a firing lockout assembly to prevent the translatable member from being actuated at an undesirable time; and (3) an emergency return button to retract the translatable member before its stroke is completed, for instance in a case where completing the stroke may cause tissue to be undesirably transected. Although features such as an articulation lever, a firing lockout assembly, and an emergency return button are not explicitly illustrated in the device 10, a person skilled in the art will recognize a variety of configurations for each feature that can be incorporated into the handle portion 105 and/or other portions of the instrument 10 without departing from the spirit of the present disclosure. In addition, the teachings of the present disclosure can be applied to different types of tissue grasping surgical instruments, including, for example, motorized devices like those described in U.S. Pat. No. 9,161,803, as well as instruments configured for use with surgical robots like those described in U.S. Pat. Pub. No. 2014/0276719. The teachings of each of these references are incorporated by reference in their entirety.

Further information on electrosurgical end effectors, jaw closure mechanisms, and electrosurgical energy-delivery surfaces are described in the following U.S. patents, all of which are incorporated by reference in their entirety and made a part of this specification: U.S. Pat. Nos. 7,381,209; 7,354,400; 7,311,709; 7,220,951; 7,189,233; 7,186,253; 7,169,147; 7,125,409; 7,087,054; 7,083,619; 7,070,597; 7,041,102; 7,011,657; 6,926,716; 6,913,579; 6,905,497; 6,802,843; 6,656,177; 6,533,784; and 6,500,176, as well as U.S. Pat. Pub. Nos. 2010/0036370 and 2009/0076506. The various embodiments disclosed in these references can be utilized and combined with the devices and methods described herein.

As noted above, it can be important to compress tissue between the jaw members concurrently with delivery of RF or other energy in order to form an effective tissue seal or weld. Transferring sufficient compressive force to the first and second jaw members 120A, 120B using a closure mechanism that acts only on a proximal portion of the jaw members, e.g., near their point of pivotable attachment to one another, can be difficult. This difficulty can be due to an inability of a closure mechanism to supply sufficient force at the proximal end of the jaw members 120A, 120B, but can also result from insufficient stiffness of the jaw members themselves. As the closure mechanism applies force to a proximal end of the first and second jaw members 120A, 120B to urge them toward one another, the tissue clamped therebetween exerts a countering force on the jaw members. The separation between the point of application of the closure mechanism force (i.e., a proximal end of the jaw members) and the countering force from tissue (i.e., acting along the length of the jaw members extending distally from the proximal end thereof) can create a moment that tends to deflect the jaw members along their length away from one another. The deflection can begin any distance away from the pivotable coupling of the jaw members and become progressively greater toward a distal end thereof. When the jaw members deflect, they transfer less of force from the closure mechanism to the tissue.

The problem of insufficient rigidity or stiffness of the jaw members 120A, 120B is often overlooked in devices similar to instrument 10 because any deflection of the jaw members 120A, 120B can be counteracted by the compression force imparted through the cams of the reciprocating member 140. In other words, as the reciprocating member 140 is advanced distally to transect tissue clamped between the jaw members 120A, 120B, the flanges 140A, 140B can more effectively urge the jaw members toward one another via cam surfaces 144A, 144B and counteract any deflection that might exist.

It can be desirable, however, to clamp tissue between jaw members 120A, 120B with sufficient force to create a good tissue seal/weld without also transecting the tissue. In such cases, distally advancing the reciprocating member 140 is not possible because it would transect the tissue. Accordingly, an alternative end effector design is needed to increase the stiffness, rigidity, or resistance to deflection of at least one of the jaw members and thereby allow sufficient compression force to be applied using only a closure mechanism that acts on a proximal end of the jaw members.

FIGS. 4-16 illustrate one embodiment of an end effector 400 having first and second jaw members 402, 404 that exhibit increased stiffness or resistance to deflection when clamping tissue therebetween. Increased stiffness can be quantified by a measure known as area moment of inertia (also known as moment of inertia of an area or second moment of area), a property of a shape that can be used to predict deflection, bending, and stress in beams. To illustrate area moment of inertia, the first and second jaw members 402, 404 of the end effector 400 can be analogized to solid rectangular beams and the coordinate system illustrated in FIG. 4 can be utilized. That is, length can be measured along a longitudinal axis L, height can be measured along an axis H that is perpendicular to the longitudinal axis L and contained within a plane in which the first and second jaw members move (e.g., pivot) relative to one another, and width can be measured along an axis W that is perpendicular to both the longitudinal axis L and the height axis H. In such an embodiment, equation (1) below can be used to solve for the area moment of inertia about the W axis. Note that deflection induced by countering force from tissue clamped between the jaw members 402, 404 is about the W axis or, put another way, is in the plane in which the first and second jaws move relative to one another (i.e., the "H-L" plane of FIG. 4).

$$\text{Area Moment of Inertia}_{Axis\,W} = \frac{\text{Width} * \text{Height}^3}{12} \quad (1)$$

While the particular geometry of the first and second jaw members 402, 404 can alter the calculation, the above equation shows that, generally speaking, beam height can have an outsized effect on resistance to deflection about a beam width axis. Accordingly, increasing a height of a jaw member (again, a dimension measured along the axis H in FIG. 4 that is perpendicular to a longitudinal axis L and contained within a plane in which the first and second jaw members move relative to one another) can create significant increases in stiffness or resistance to deflection from the types of forces that are experienced when tissue is clamped between the jaw members.

Given this result, in some embodiments the end effector 100 can be modified by increasing the height of at least one of the first and second jaw members 120A, 120B to increase stiffness. In certain embodiments, however, it can be desirable to eliminate or minimize any increase in the overall height of the end effector, for example, to ensure that the end effector can be introduced through a trocar, body passageway, or other opening during a procedure. With the design of end effector 100, increasing the height of one or more of the first and second jaw members 120A, 120B can result in a significant increase in the overall height of the end effector.

The end effector 400 shown in FIGS. 4-16 provides one solution to this problem by nesting the first and second jaw members 402, 404 within one another such that one or both jaw members can have increased height while an overall height of the end effector is minimized. For example, and as can be seen in the figures, the first and second jaw members 402, 404 can each have a height measured at a proximal end thereof that is greater than half of an overall height $H_0$ (see FIGS. 6 and 13) of the end effector 400, while at a distal end of the end effector a sum of the heights of the first and second jaw members can be approximately equal to the overall height $H_0$ (see FIG. 4). As is explained in more detail below, this configuration can be accomplished in a variety of manners.

Figure 4:
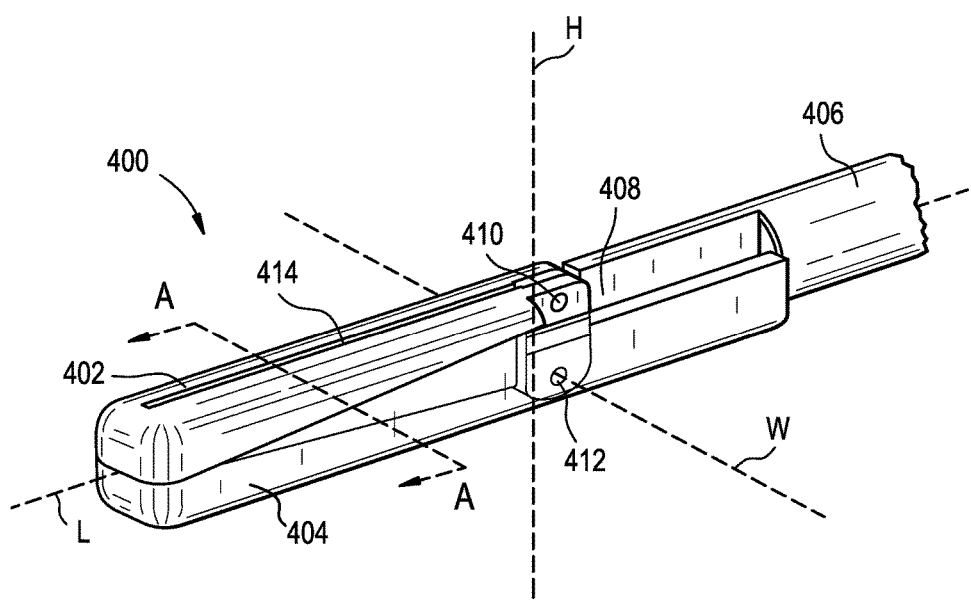
FIG. 4 is a perspective view illustration of one embodiment of a surgical end effector according to the teachings of the present disclosure.

Turning to FIG. 4, the end effector 400 can be coupled to a shaft 406 that extends proximally to, for example, an actuator of the device or instrument carrying the end effector. In some embodiments, the shaft 406 can be a distal extension of a drive screw or other rotating and/or translating member and can be coupled to a closure mechanism 408 of the end effector 400. The closure mechanism 408 can be pivotably coupled to the first jaw member 402, e.g., by a pin 410, such that distal advancement and proximal retraction of the closure mechanism can cause movement of the first jaw member 402 relative to the second jaw member 404, e.g., relative pivoting in the plane defined by the L axis and the H axis about a pivotable coupling 412 between the first and second jaw members.

Figure 5:
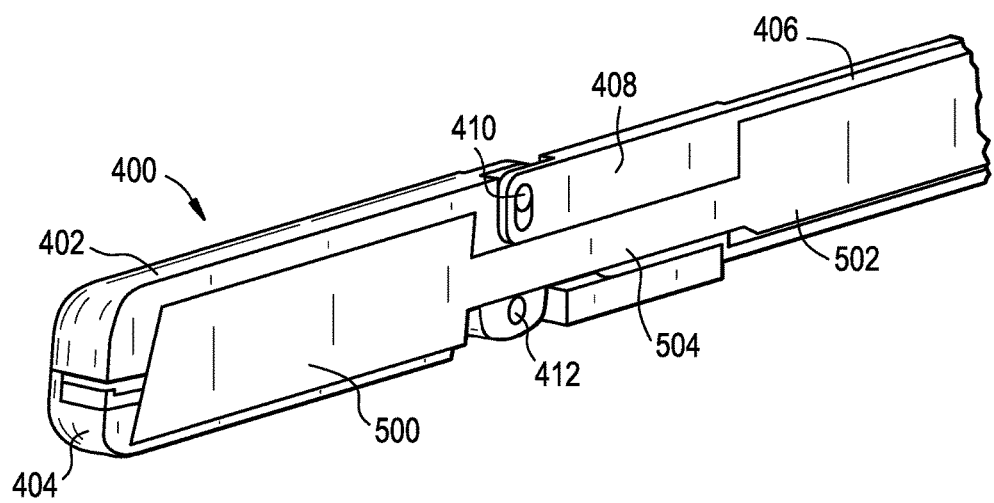
FIG. 5 is a perspective cross-sectional view of the end effector of FIG. 4 taken along the plane defined by the H axis and the L axis.

The end effector 400 can also include a reciprocating cutting element 500, as shown in FIG. 5. The cutting element 500 can be disposed in a middle portion of the end effector 400 and can be configured to ride proximally and distally within a track or slot 414 formed in one or more of the first jaw member 402 and the second jaw member 404. The cutting element 500 can be coupled to a second shaft 502 by a connector 504 such that movement of the cutting element 500 can be controlled at a proximal end of the surgical device. The second shaft 502, which can be, for example, a second drive screw or other rotating and/or translating member, can be received within a lumen of the shaft 406 in the illustrated embodiment. The connector 504 can extend between the cutting element 500 and the shaft 502 and can be configured to avoid interfering with the pivotable couplings 410, 412 between the closure mechanism 408, the first jaw member 402, and the second jaw member 404. In other embodiments, one or more shafts, beams, linkages, or other structures can be utilized to couple the cutting element 500 to a proximal actuator. Further, because the cutting element 500 is not relied upon to impart additional compressive force to tissue, it can be formed in some embodiments as a planar, blade-like member that does not include the flanges 140A, 140B illustrated in FIG. 3. In other embodiments, however, a similar configuration to the reciprocating member 140 of FIG. 3 can be utilized to provide greater strength and/or stiffness to the cutting element 500 itself and/or to impart additional compressive force to tissue in the manner described above.

Figure 6:
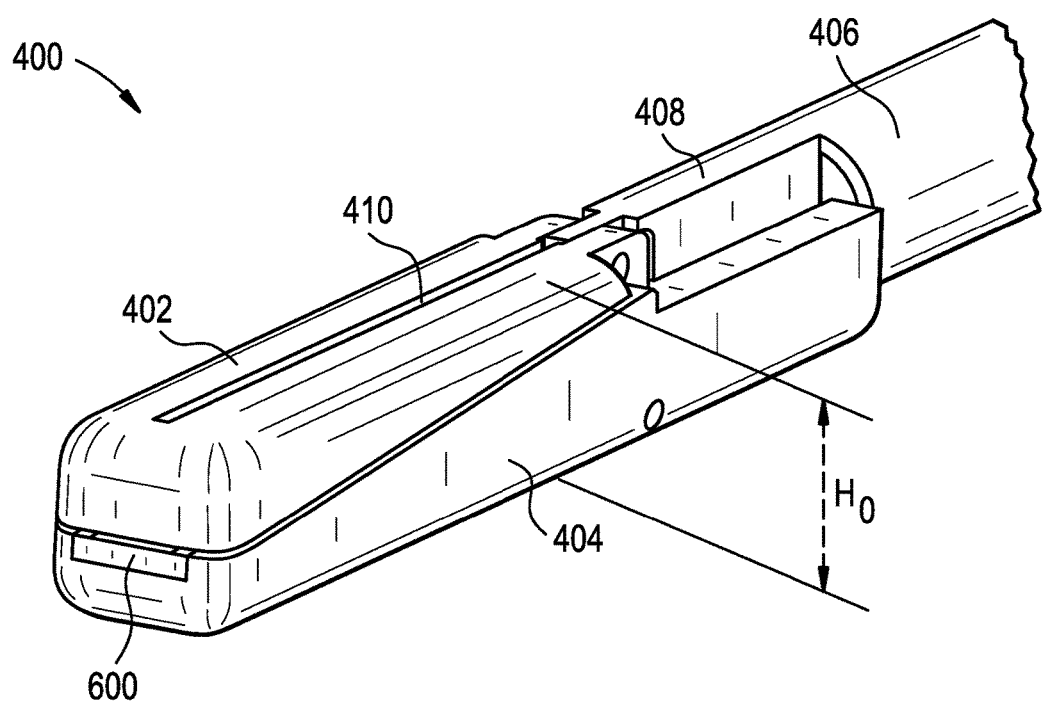
FIG. 6 is an alternative perspective view illustration of the end effector of FIG. 4.

The end effector 400 may further include one or more electrodes or other energy delivery structures coupled thereto or formed thereon. As shown in FIG. 6, the end effector 400 can include an electrode or other energy delivery structure 600 formed on a tissue-contacting surface of the second jaw member 404. The electrode 600 can be configured to deliver energy to tissue in the manner of the energy delivery structure 175B discussed above. Moreover, similar to the end effector 100 described above, a complementary electrode or energy delivery structure can be formed on a tissue-contacting surface of the first jaw member 402. These electrodes can be configured in mono- or bi-polar configurations and can include additional layers of, for example, electrically resistive or variably resistive (e.g., based on temperature, etc.) materials disposed thereon, as described above. In the illustrated embodiment, the first jaw member 402 can be formed from an electrically conductive material and the entire first jaw member can serve as an energy delivery structure. For example, RF or other electrical energy can be passed from the electrode 600 disposed on the second jaw member 404 to the first jaw member 402 (or vice versa) and can pass through any tissue grasped therebetween.

Figure 7:
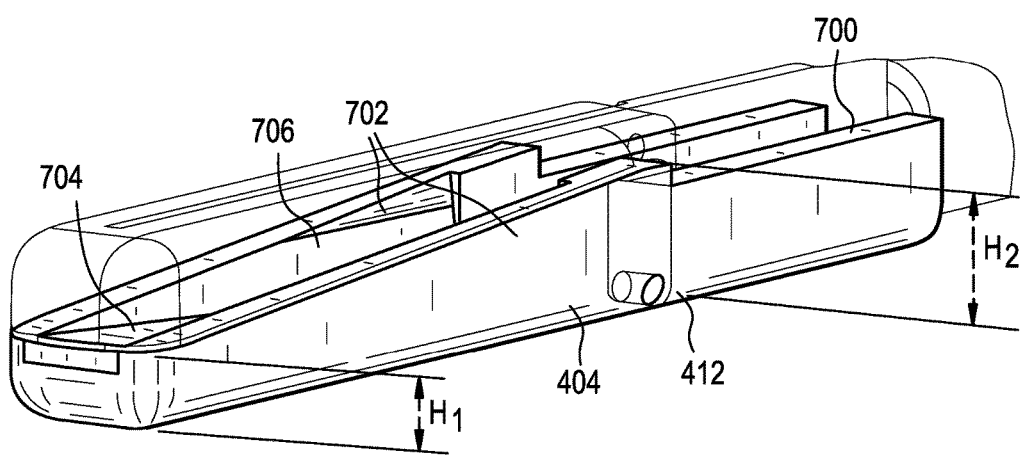
FIG. 7 is a detail view of a stationary jaw member of the end effector of FIG. 4 with other components shown in phantom.

FIG. 7 illustrates the second jaw member 404 in greater detail. The second jaw member 404 can, in some embodiments, be a stationary jaw member that does not pivot relative to, for example, the shaft 406 or other component that couples the end effector to a proximal actuator. In other embodiments, however, the second jaw member 404 can be configured to move about any of the L, H, and W axes to provide, for example, articulation of the end effector 400 and/or closure of the jaw members 402, 404. In some embodiments, the second jaw member 404 can include a proximal portion 700 that extends proximally from the point of pivotable coupling 412 with the first jaw member 402. This proximal portion 700 can, for example, be configured to at least partially surround and house a translating closure mechanism 408, cutting element 500, or other component of the end effector 400.

In some embodiments, the second jaw member 404 can have a height that varies along a length thereof. For example, a first height $H_1$ at a distal end of the second jaw member can be equal to approximately one half of an overall height $H_0$ of the end effector 400, while a second height $H_2$ at a proximal end or portion of the second jaw member can be greater than one half of the overall height $H_0$. The height of the second jaw member 404 can vary along its length in a number of ways. In some embodiments, for example, the height of the second jaw member 404 can taper from a proximal end to a distal end thereof, as shown in FIG. 7. In other embodiments, the height can change in one or more discrete steps, or can change along a profile having any of a variety of shapes that generally decrease from the height $H_2$ to the height $H_1$ over the length of the second jaw member 404.

As noted above, the first and second jaw members 402, 404 can be configured to nest within one another in order to minimize any increase in the overall height $H_0$ of the end effector that might result from increasing their respective heights. While the configuration can be reversed, the embodiment of FIG. 7 illustrates that the second jaw member 404 includes sidewalls 702 that extend upward along the H axis from a tissue-contacting surface 704 formed on the second jaw member. The sidewalls gradually increase in height from the distal height $H_1$ to the proximal height $H_2$ described above and therefore help to increase the stiffness or resistance to deflection of the second jaw member 404. The sidewalls 702 also give the second jaw member 404 a generally "U" shaped cross-section with a cavity 706 extending between the sidewalls 702. This "U" shape can extend to the proximal portion 700 such that the closure mechanism or other actuator 408 for moving the first and second jaw members relative to one another can be disposed within the cavity 706.

Figure 8:
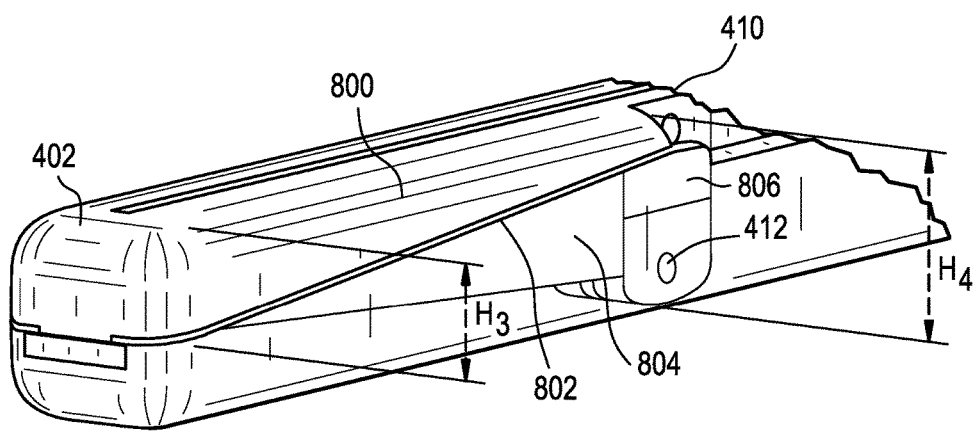
FIG. 8 is a detail view of a movable jaw member of the end effector of FIG. 4 with other components shown in phantom.

FIG. 8 illustrates the complementary first jaw member 402 that is configured to nest with the second jaw member 404 such that an overall height $H_0$ of the end effector 400 is minimized. The first jaw member 402 can also have a height that varies along a length thereof. For example, a first height $H_3$ at a distal end of the first jaw member can be equal to approximately one half of an overall height $H_0$ of the end effector 400, while a second height $H_4$ at a proximal end or portion of the first jaw member can be greater than one half of the overall height $H_0$. The height of the first jaw member 404 can vary along its length in a number of ways, for example via a straight line taper as shown, or any of a variety of other shapes or profiles.

The first jaw member 402 can include a first portion 800 that can be configured to align with an outer profile of the second jaw member 404. The first portion 800 can have, for example, an outer width that substantially aligns with an outer width of the second jaw member 404. Accordingly, the first portion 800 can include an outer edge 802 having a profile that is complementary to a profile of the sidewalls 702 of the second jaw member 404.

The first jaw member 402 can also include a second portion 804 that is configured to extend into the cavity 706 formed between the sidewalls 702 of the second jaw member 404. In some embodiments, the height of the first jaw member 402 can increase from a distal end to a proximal end thereof along the second portion 804.

The first jaw member 402 can also include a proximal portion 806 that can include, for example, one or more bores to receive pins for pivotably coupling the first jaw member to other components. The one or more bores can be positioned, for example, at the pivotable coupling 412 between the first jaw member 402 and the second jaw member 404, as well as at the pivotable coupling 410 between the first jaw member and the closure mechanism or other actuator 410. As is explained in more detail below, the bores can be positioned as far apart as possible to maximize the mechanical advantage of the closure mechanism 408.

Figure 9:
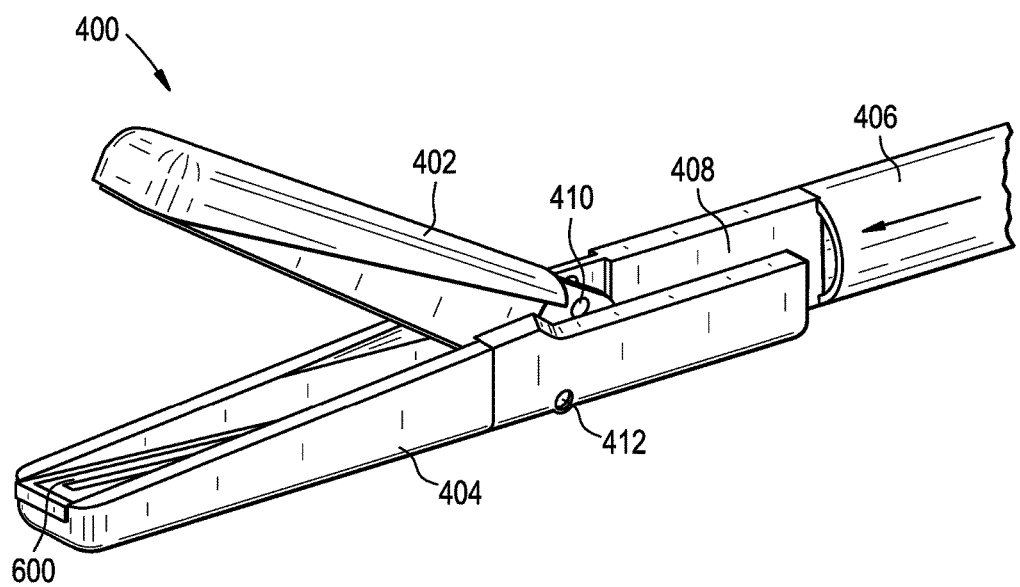
FIG. 9 is a perspective view illustration of the end effector of FIG. 4 in an open position.

The closure mechanism or actuator 408 is illustrated in more detail in FIGS. 9-12. FIG. 9 illustrates the end effector 400 with the first and second jaw members 402, 404 in an open configuration that can be used to position tissue between the jaw members before clamping, sealing/welding, transecting, etc. In this configuration, the shaft or drive screw 406 can be retracted proximally, which in turn can retract the closure mechanism 408 proximally. Because the closure mechanism 408 is pivotably coupled to the first jaw member 402, and the first jaw member is pivotably coupled to the second jaw member 404, the proximal retraction of the closure mechanism 408 can cause the first jaw member 402 to pivot away from the second jaw member 404 about the pivotable coupling 412.

Figure 10:
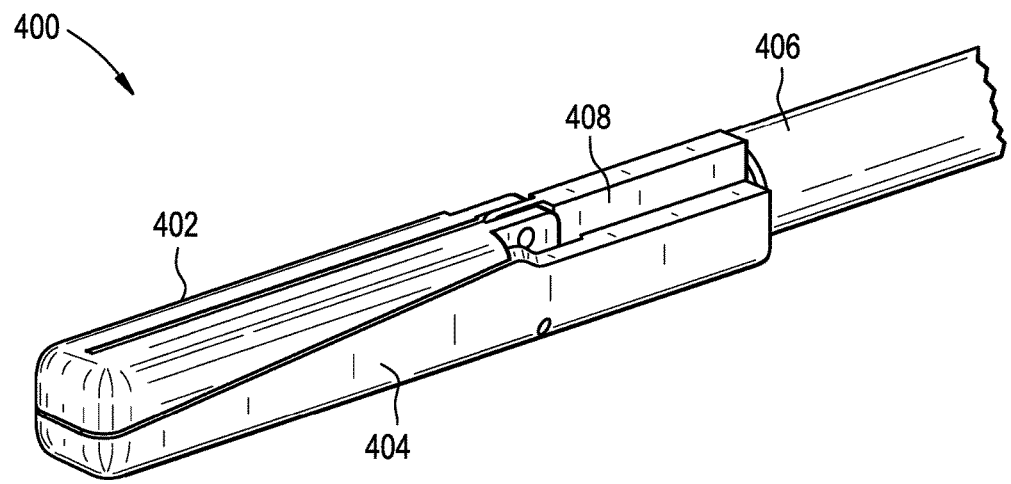
FIG. 10 is a perspective view illustration of the end effector of FIG. 4 in a closed position.

To move the first and second jaw member 402, 404 from the open configuration to a closed configuration, as illustrated in FIG. 10, the shaft 406 can be advanced distally. As noted above, the shaft 406 can be a drive or lead screw or other rotating and/or translating member that couples the end effector 400 to a proximal actuator of the surgical instrument. The shaft 406 can be driven in some embodiments by manually applied force from a user, e.g., via a trigger or lever like the lever arm 128 of FIG. 1. In other embodiments, however, the shaft can be driven by an electric motor disposed in, e.g., a housing at a proximal end of the surgical instrument and controlled by a user via, for example, a button or other trigger. As noted above, still other embodiments can be configured for control by a surgical robot, e.g., via a coupling between the shaft and a robot arm or via a robotic interface for operating a handle, trigger, switches, etc. of an instrument. In any of these various control configurations, distal advancement of the shaft 406 can cause distal advancement of the closure mechanism or actuator 408. This movement of the closure mechanism 408 can cause the first jaw member 402 to pivot towards the second jaw member 404 about the pivotable coupling 412 to clamp any tissue disposed therebetween.

Figure 11:
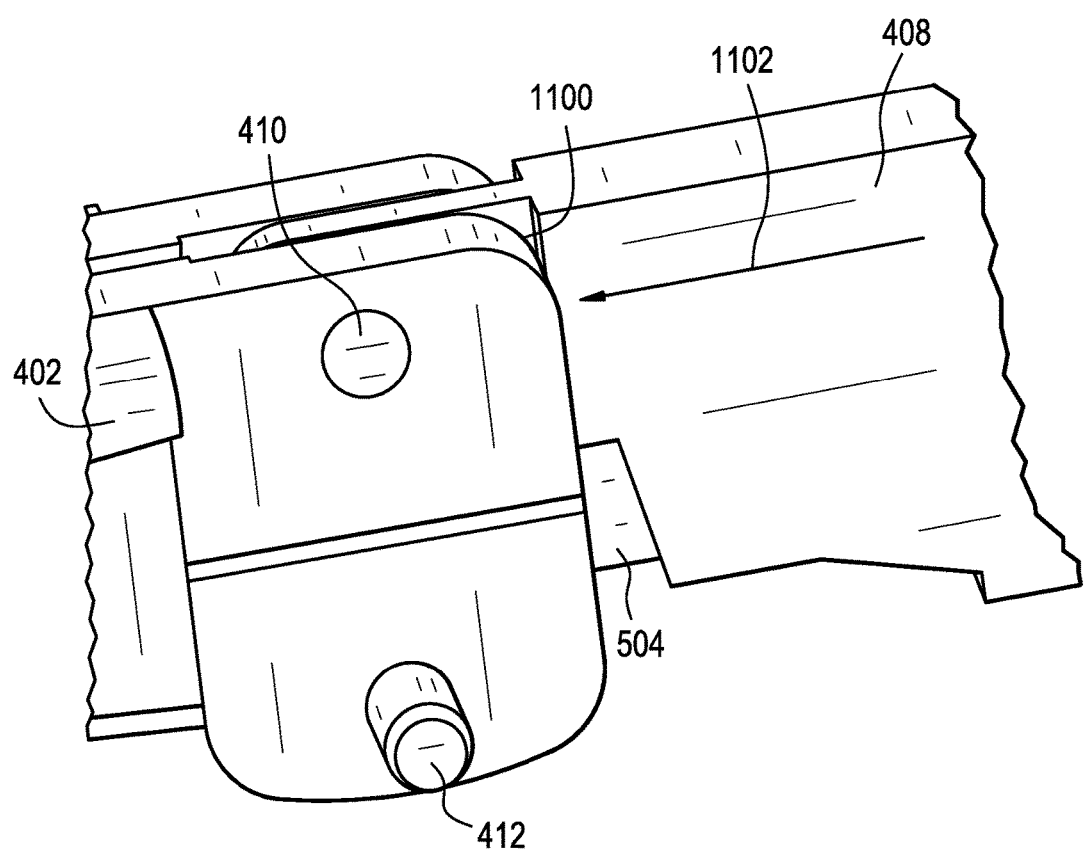
FIG. 11 is a detail view of a pivotable coupling between an actuator and jaw members in the end effector of FIG. 4.
Figure 12:
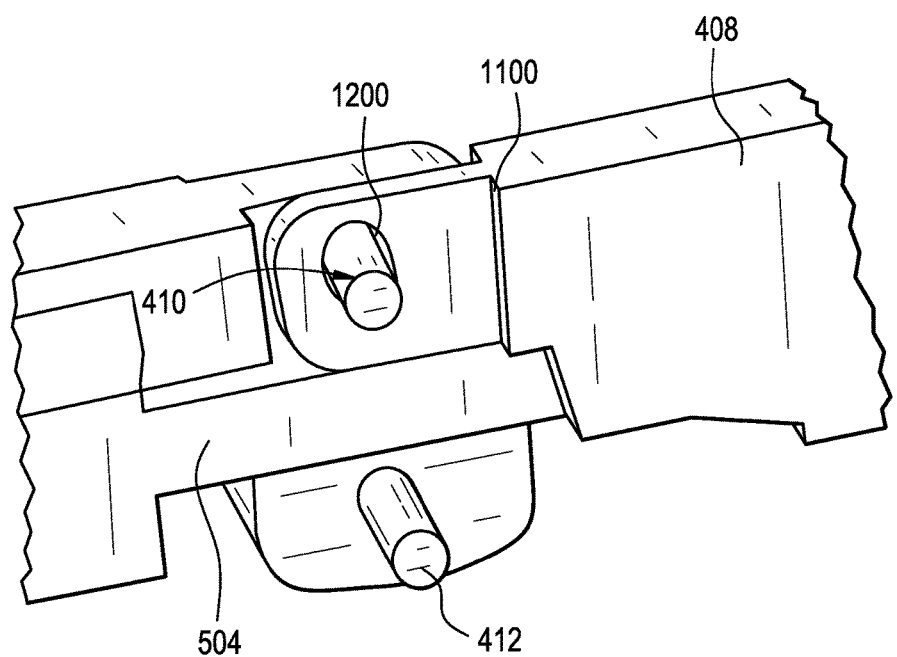
FIG. 12 is an alternative detail view of the pivotable coupling shown in FIG. 11.

FIGS. 11 and 12 illustrate the coupling of the first jaw member 402, second jaw member 404, and closure mechanism 408 in more detail. Referring to FIG. 11, the planar distal-facing surface 1100 of the closure mechanism 408 can be seen acting on a planar proximal-facing surface of the first jaw member 402. The planar distal-facing surface 1100 can be formed, for example, as a shoulder or shelf extending from a distal portion of the closure mechanism that is pivotably coupled to the first jaw member at the position 410. The planar distal-facing surface 1100 can be advantageous because it provides a larger surface area over which force can be transmitted to the first jaw member 402, illustrated by arrow 1102, to urge the first jaw member toward the second jaw member 404, thereby compressing tissue between the jaw members.

The closure mechanism can be further enhanced by separating the pivoting pins 410, 412 as much as possible to create a larger mechanical advantage in the mechanism. More particularly, the planar distal-facing surface 1100 can be positioned toward an upper end of the first jaw member 402, while the pivotable coupling 412 between the first and second jaws 402, 404 can be positioned toward a lower end of the first jaw member. Accordingly, the application of distal force 1102 can create a maximum moment about pivotable coupling 412 to urge the first jaw member 402 toward the second jaw member 404.

With the configuration of the first jaw member 402 and the planar distal-facing surface 1100 of the closure mechanism 408, it is possible that the first jaw member can be prevented from pivoting away from the second jaw member 404 when the closure mechanism is retracted proximally. As shown in FIG. 12, this issue can be addressed by providing an enlarged through-hole 1200 in the closure mechanism 408 that has clearance around the pivotable coupling pin 410 that connects the closure mechanism 408 to the first jaw member 402. The clearance around the pivotable coupling pin 410 can allow the planar distal-facing surface 1100 of the closure mechanism 408 to retract proximally and separate from the planar proximal-facing surface of the first jaw member 402 as the closure mechanism 408 is retracted proximally. The separation between the surface 1100 and the first jaw member 402 can allow the first jaw member to pivot about the pin 410 and the pin 412, thereby moving the first jaw member 402 towards the open configuration shown, for example, in FIG. 9. In certain embodiments, a spring can be incorporated into the closure mechanism 408 to eliminate any play between the closure mechanism, shaft 406, and first jaw member 402, while allowing the above-described separation during retraction.

Figure 13:
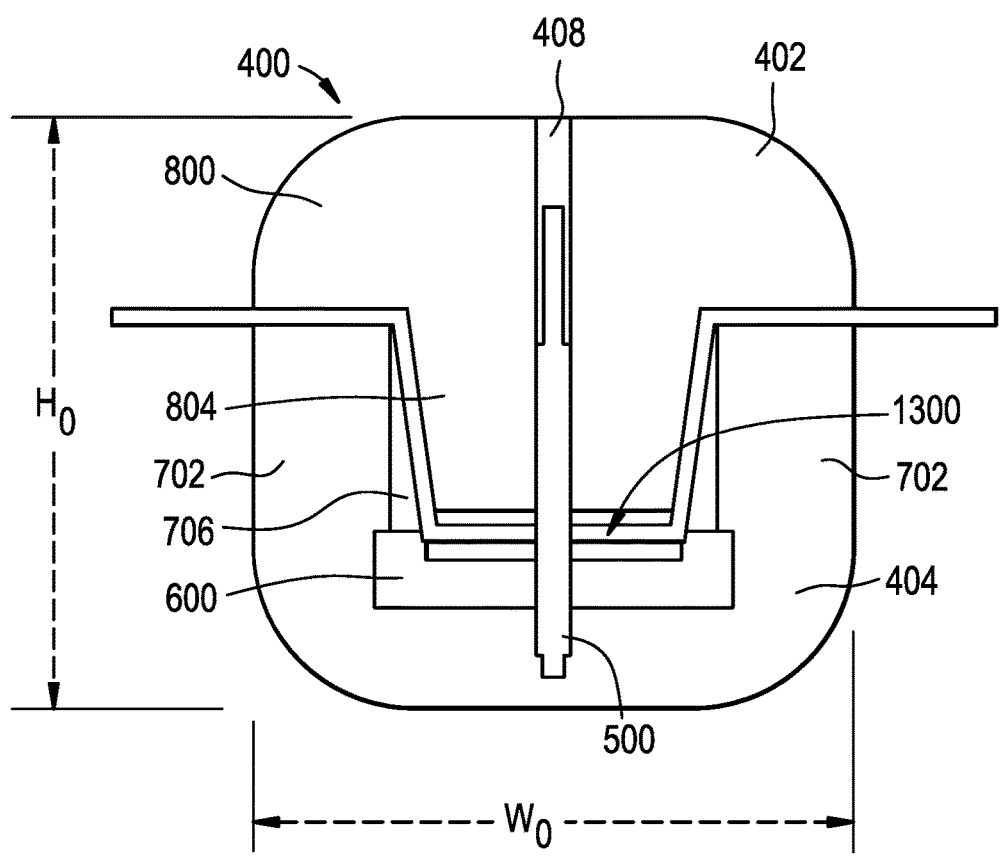
FIG. 13 is a front cross-sectional view taken along the line A-A of the end effector of FIG. 4 in a closed position clamping tissue between jaw members.

FIG. 13 illustrates a front cross-sectional view of the end effector 400 in the closed position in which tissue 1300 is clamped between the first jaw member 402 and the second jaw member 404. The figure illustrates how both the first jaw member 402 and the second jaw member 404 can have an increased height (i.e., dimension measured along the H axis of FIG. 4) along at least a portion thereof without causing an increase in the overall height $H_O$ of the end effector 400. In the illustrated configuration, an overall height $H_O$ of at least a portion of the end effector can be greater than an overall width $W_O$ of at least a portion of the end effector (i.e., dimension measured along the W axis of FIG. 4). Further, the height of at least a portion of each jaw member 402, 404 can also be greater than a width of at least a portion thereof.

FIG. 13 also illustrates how tissue can be deformed and stretched as it is clamped between the first and second jaw members 402, 404. This can be a result of the narrowed second portion 804 of the first jaw member 402 urging the tissue 1300 into the cavity 706 formed between the sidewalls 702 of the second jaw member 404. Stretching and deforming the tissue 1300 in this manner can have a number of advantages. For example, it can aid in grasping tissue, as well as form a better quality tissue seal or weld when RF electrical or other energy is applied from, for example, the electrode 600 to the tissue. Better seal quality can be achieved because the one or more layers of tissue 1300 captured between the first and second jaw member 402, 404 can more effectively be forced into contact with one another when stretched into a thinner, more planar configuration. Moreover, tensioning the one or more layers of tissue 1300 can allow for more efficient and better quality transection by the cutting element 500, in embodiments in which transection is desired. The increased tension of the tissue can help pass the leading edge of the cutting element 500 through the tissue, rather than bunching tissue around the leading edge. It should be noted that a size of gaps between, for example, the sidewalls 702 of the second jaw member 404 and the second portion 804 of the first jaw member 402 can be adjusted to accommodate different thicknesses of tissue 1300 and permit closing of the jaw members.

Figure 2:
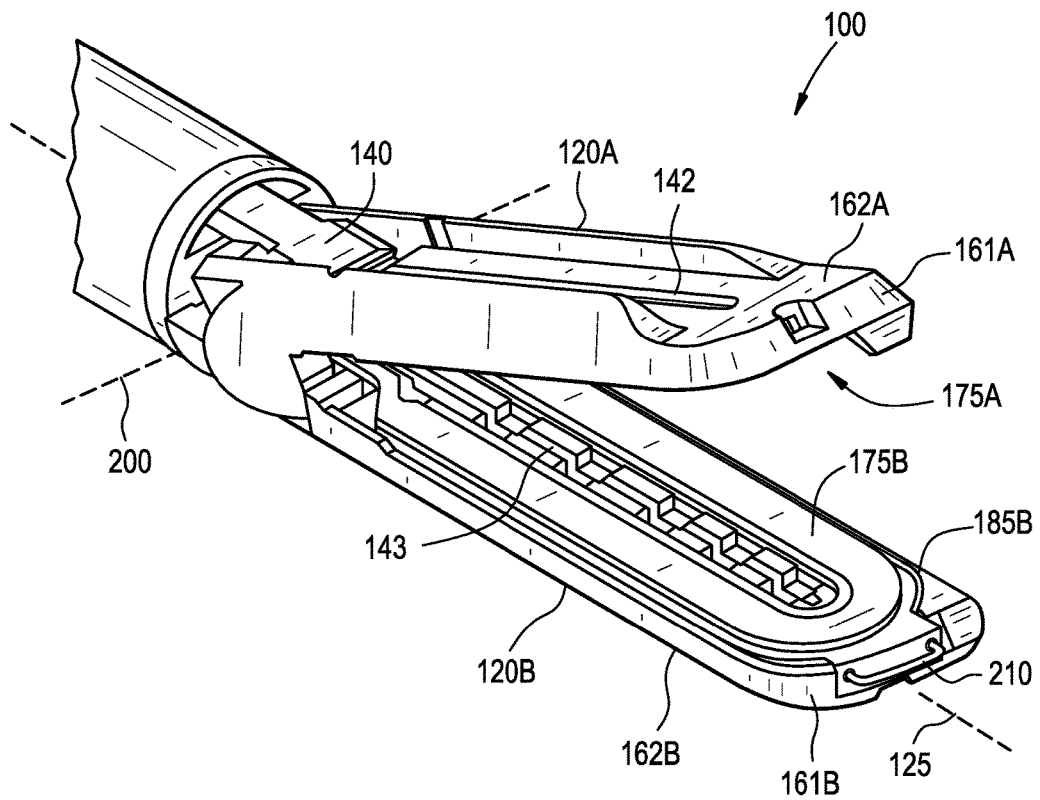
FIG. 2 is a detail view of an end effector of the device of FIG. 1.

Also shown in FIG. 13 is the increased contact area between the tissue 1300 and the tissue-contacting surfaces of the first and second jaw members 402, 404 in comparison to a typical end effector similar to end effector 100 in FIG. 1. In the typical arrangement of end effector 100 in FIG. 1, the first and second jaw members 120A, 120B include planar tissue-contacting surfaces that define a neutral plane therebetween in which tissue is disposed. In FIG. 2, for example, the neutral plane is defined by the longitudinal axis 125 and the perpendicular axis 200 that passes through the pivotable coupling of the first and second jaw members 120A, 120B. Tissue disposed between the jaw members 120A, 120B is laid flat (i.e., coplanar with the neutral plane) and therefore contacts only the opposing tissue-contacting surfaces of the first and second jaw members, i.e., the surfaces upon which energy delivery structures 175A, 175B are disposed.

In FIG. 13, the one or more layers of tissue 1300 are in contact with the corresponding upward- and downward-facing surfaces of the first and second jaw members 402, 404. They are also, however, in contact with the inner and upper surfaces of the sidewalls 702 on the second jaw member 404, the bottom surfaces of the first portion 800 of the first jaw member 402, and the sidewalls of the second portion 804 of the first jaw member 402. Accordingly, in some embodiments the electrode or other energy delivery structure 600 can be extended from the planar configuration shown to a "U" shaped configuration that covers the sidewalls 702 of the second jaw member 404. In still other embodiments, and as noted above, one or more of the first and second jaw member 402, 404 can be formed of an electrically conductive material and configured to be an electrode or other energy delivery structure. In such an embodiment, all of the surface area of the first jaw member 402 and the second jaw member 404 contacting the tissue can be configured to deliver energy thereto.

The above described embodiment of an end effector 400 can provide pivoting jaw members that have increased stiffness to allow for sufficient compression to seal and/or weld tissue without the use of a transecting element that clamps the jaws together as it advances distally through tissue. The increased stiffness of the jaw members can be accomplished by increasing a height along at least a portion thereof, i.e., a dimension that is perpendicular to a longitudinal axis of the jaw member and contained within a plane in which the jaw members move relative to one another. A height of both jaw members can be increased along at least a portion thereof, or a height of one jaw member along at least a portion thereof can be increased relative to that of another to increase stiffness of one jaw member relative to the other. Jaw members of the type described herein can be coupled with a closure mechanism or actuator that transfers force to the jaw members via a planar distal-facing surface so as to sufficiently compress tissue between the jaw members for sealing and/or welding. Moreover, the jaw members can be configured to nest within one another such that an overall height of the end effector is minimized. Configuring the end effectors to nest or otherwise interface or overlap with one another in accordance with the teachings provided herein can also tension tissue and provide more effective sealing and transection by exposing more tissue surface area to energy delivery structures.

Each of the jaw members can have a variety of shapes, sizes, and configurations in view of the disclosure provided herein. For example, in some embodiments the device can be scaled to a size suitable for use in open surgery, while in other embodiments the device can be sized for introduction through a trocar cannula, access port, or other reduced-size passage during a minimally invasive surgical procedure. Regardless of the size of the particular device, in some embodiments a proximal height of at least one of the first and second jaw members of the end effector can be greater than a distal height thereof. Moreover, a height at a midpoint along a length of the at least one jaw member can be greater than a distal height of the jaw member and less than a proximal height of the jaw member. In certain embodiments, overall heights of the first and second jaw members can be approximately in the range of about 3 millimeters to about 15 millimeters. By way of further example, in some embodiments a length of an end effector according to the teachings of the present disclosure can be approximately in the range of about 12 millimeters to about 60 millimeters, a width of the end effector can be approximately in the range of about 3 millimeters to about 15 millimeters, and an overall height of the end effector can be approximately in the range of about 3 millimeters to about 15 millimeters.

Figure 14:
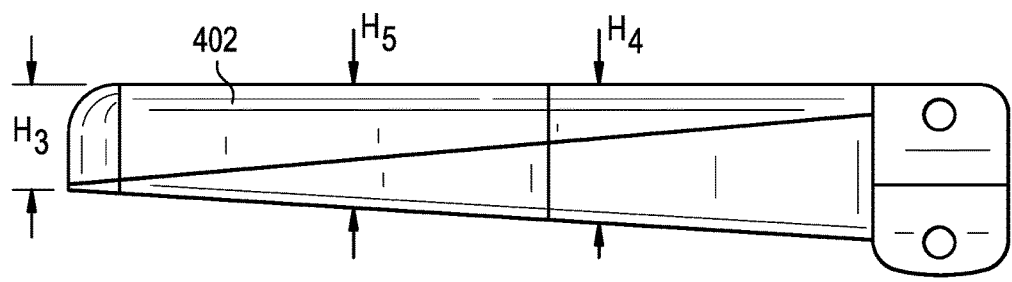
FIG. 14 is a side view of the movable jaw member of the end effector of FIG. 4.
Figure 15:
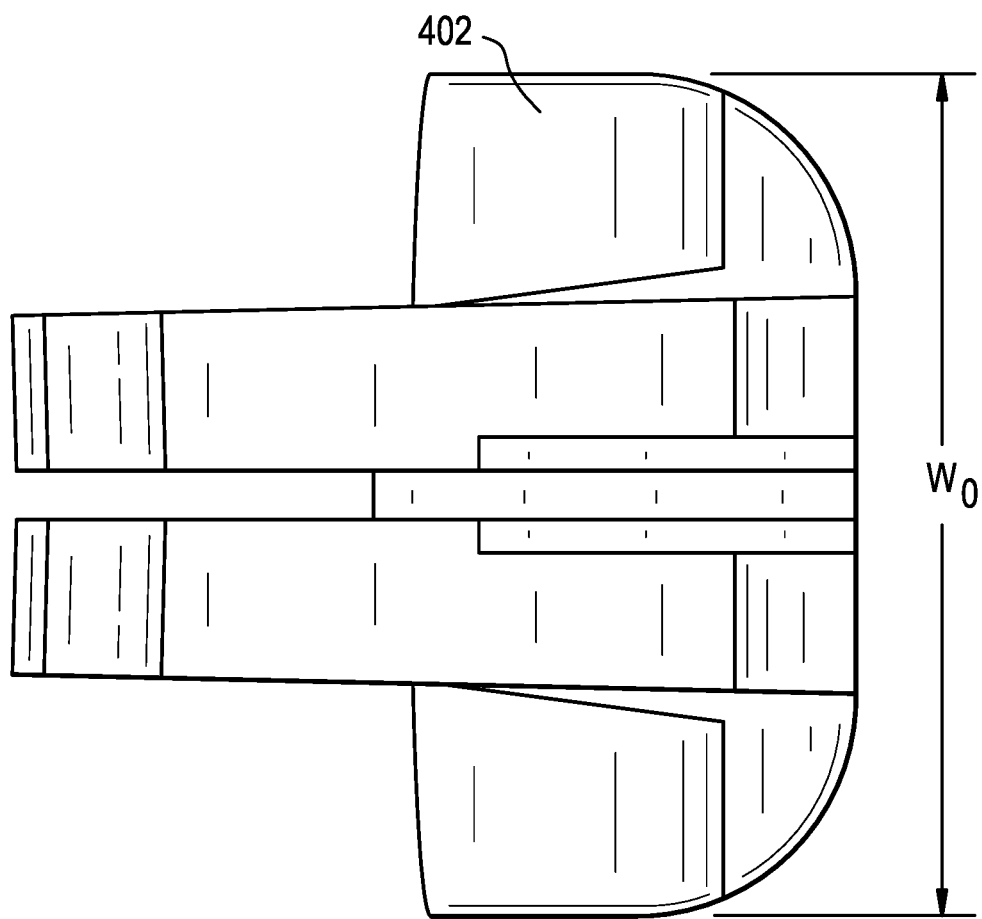
FIG. 15 is a rear view of the movable jaw member of the end effector of FIG. 4.
Figure 16:
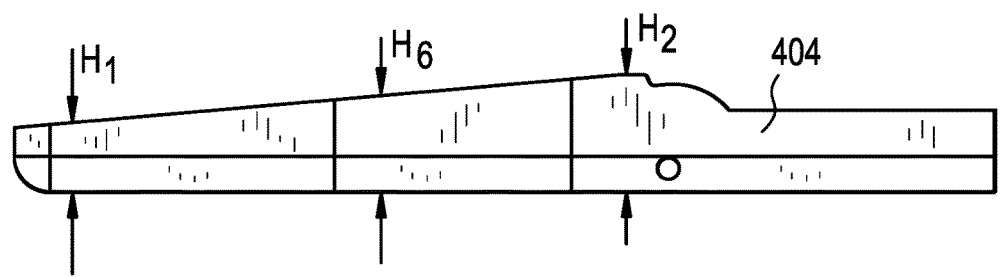
FIG. 16 is a side view of the stationary jaw member of the end effector of FIG. 4.

FIGS. 14-16 provide exemplary dimensions for the first and second jaw members 402, 404 of the end effector 400. As noted above, the end effector 400 can be varied in size and shape according to intended use, etc., and the noted dimensions are exemplary. FIG. 14 illustrates that the first jaw member 402 can have a height $H_3$ at a distal end thereof that is about 0.2169 inches (5.51 millimeters), a height $H_4$ near a proximal end thereof that is about 0.31 inches (7.87 millimeters), and a height $H_5$ near a mid-point along a length thereof that is about 0.2676 inches (6.8 millimeters). FIG. 15 illustrates that an exemplary overall width of the first jaw member 402 can be about 5 millimeters, and the second jaw member can have a similar overall width. FIG. 16 provides exemplary height dimensions for the second jaw member 404. In particular, the second jaw member 404 can have a height $H_1$ at a distal end thereof that is about 0.1788 inches (4.54 millimeters), a height $H_2$ near a proximal end thereof that is about 0.2995 inches (7.61 millimeters), and a height $H_6$ near a mid-point along a length thereof that is about 0.2444 inches (6.21 millimeters).

The nesting configuration of the end effector jaw members that allows a central portion of the first jaw member to sit within a recess formed in a central portion of the second jaw member can allow a portion of both the first jaw member and the second jaw member, e.g., a central portion of the first jaw member and a peripheral portion of the second jaw member, to have a height that is greater than half of an overall height of the end effector. Based on the exemplary dimensions provided above, a difference in the height of the peripheral portion of the second jaw member between the proximal and distal end thereof can be approximately in the range of about 2 millimeters to about 5 millimeters and, in some embodiments, can be about 3 millimeters. In other embodiments, however, greater or lesser angles of slope between the proximal and distal ends of the second jaw member are possible. In addition, the peripheral portion of the first jaw member can have a complementary, opposite difference in heights between its proximal and distal ends (as shown, for example, in FIGS. 4 and 6-10).

Figure 17:
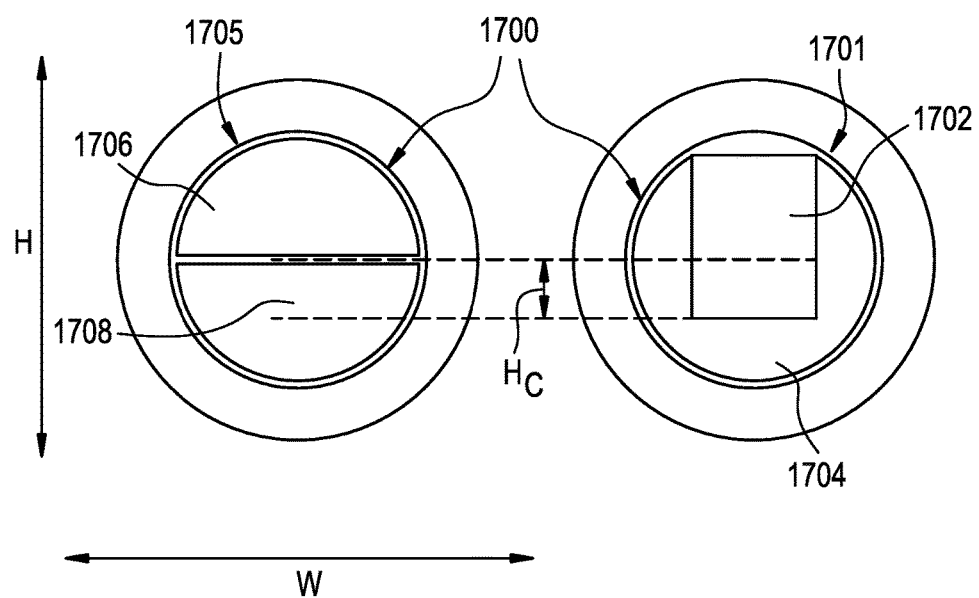
FIG. 17 is a schematic front view illustration comparing a prior art surgical instrument to one embodiment of a surgical end effector according to the teachings of the present disclosure.

The surgical instrument end effectors described herein can provide a number of advantages over prior art end effectors. In some embodiments, one such advantage can be an increase in end effector jaw stiffness without increasing an overall size of the end effector such that the end effector can be used within the confines of a given operating envelope, e.g., an operating envelope defined by a cannula diameter (e.g., a 5 millimeter trocar cannula) or other passage size through which the instrument is to be passed. FIG. 17 illustrates one embodiment of an end effector 1701 according to the teachings of the present disclosure and compares it to a prior art end effector 1705. As shown, end effectors 1701, 1705 both fit within the cannula envelope 1700 (i.e., they both can be passed through the cannula successfully). First jaw member 1702 of the end effector 1701, however, can have an increased height relative to corresponding jaw member 1706 of the prior art end effector 1705, as shown by measurement $H_C$. Moreover, because the second jaw member 1704 of the end effector 1701 is configured to surround and nest with the first jaw member 1702, it can also have an increased height relative to the height of the corresponding jaw member 1708. As explained above, this increased height (measured in the direction of the height axis H) can increase the stiffness of the jaw members and permit greater compressive forces to be applied to tissue grasped therebetween. Accordingly, end effectors described herein can provide increased stiffness relative to prior art end effectors for a given operating envelope size.

Figure 18:
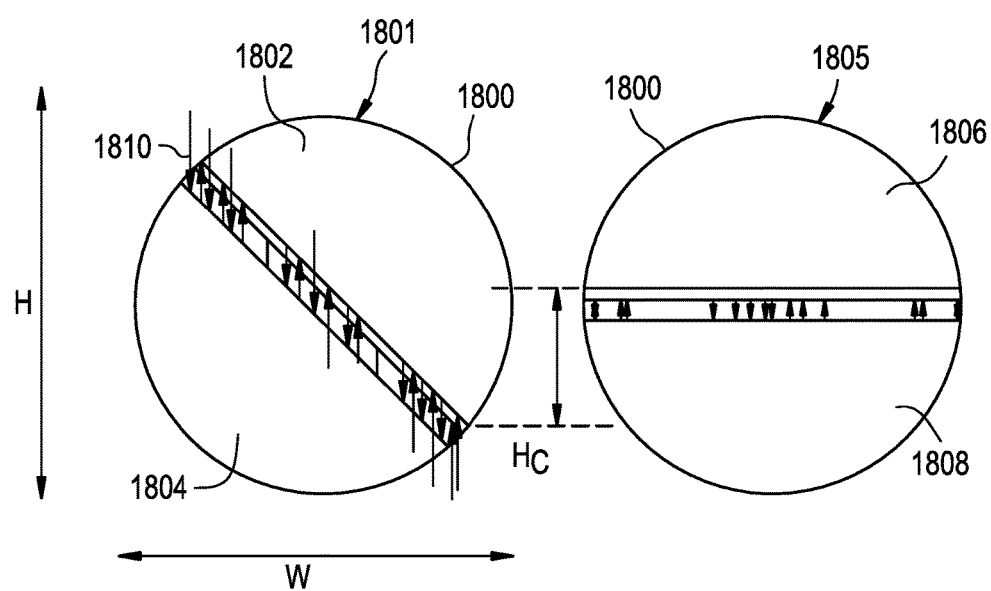
FIG. 18 is a schematic front view illustration comparing a prior art surgical instrument to another embodiment of a surgical end effector according to the teachings of the present disclosure.

FIGS. 18-22 illustrate another embodiment of an end effector 1801 having increased stiffness for a given size relative to a prior art end effector 1805. In contrast to the end effector 400 described above, the end effector 1801 can provide increased jaw member height (as measured along the H axis) by orienting its tissue-facing surfaces such that they are transverse to an axis W along which width is measured. The change in height $H_C$ (measured along the height axis H) between the first jaw member 1802 of the end effector 1801 and the corresponding jaw member 1806 of the prior art jaw member 1805 is shown in the figure. A corresponding difference in height can also be achieved with regard to the second jaw member 1804 and corresponding jaw member 1808 of the prior art end effector 1805. As explained above, the increased height of the jaw members can increase their stiffness relative to forces applied along the height axis H. FIG. 18 shows an example of such forces with arrows 1810, which represent force that can be applied by tissue as it is grasped between the jaw members. Due to the increased height of the jaw members 1802, 1804 relative to the prior art jaw members 1806, 1808, the jaw members 1802, 1804 can deflect less than the jaw members 1806, 1808 and more effectively transfer force from a closure mechanism to tissue.

Figure 19:
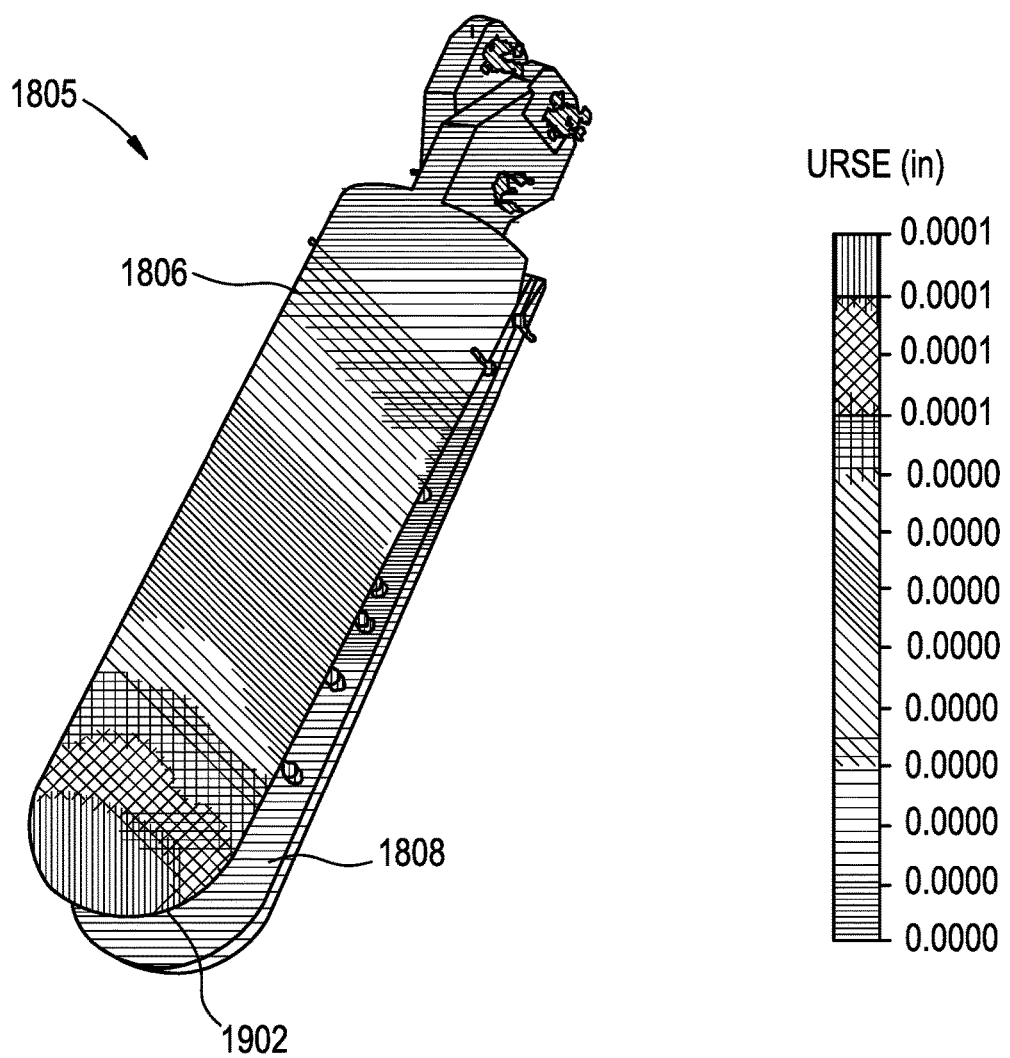
FIG. 19 is an illustration of simulated deflection of the prior art surgical instrument shown in FIG. 18.
Figure 20:
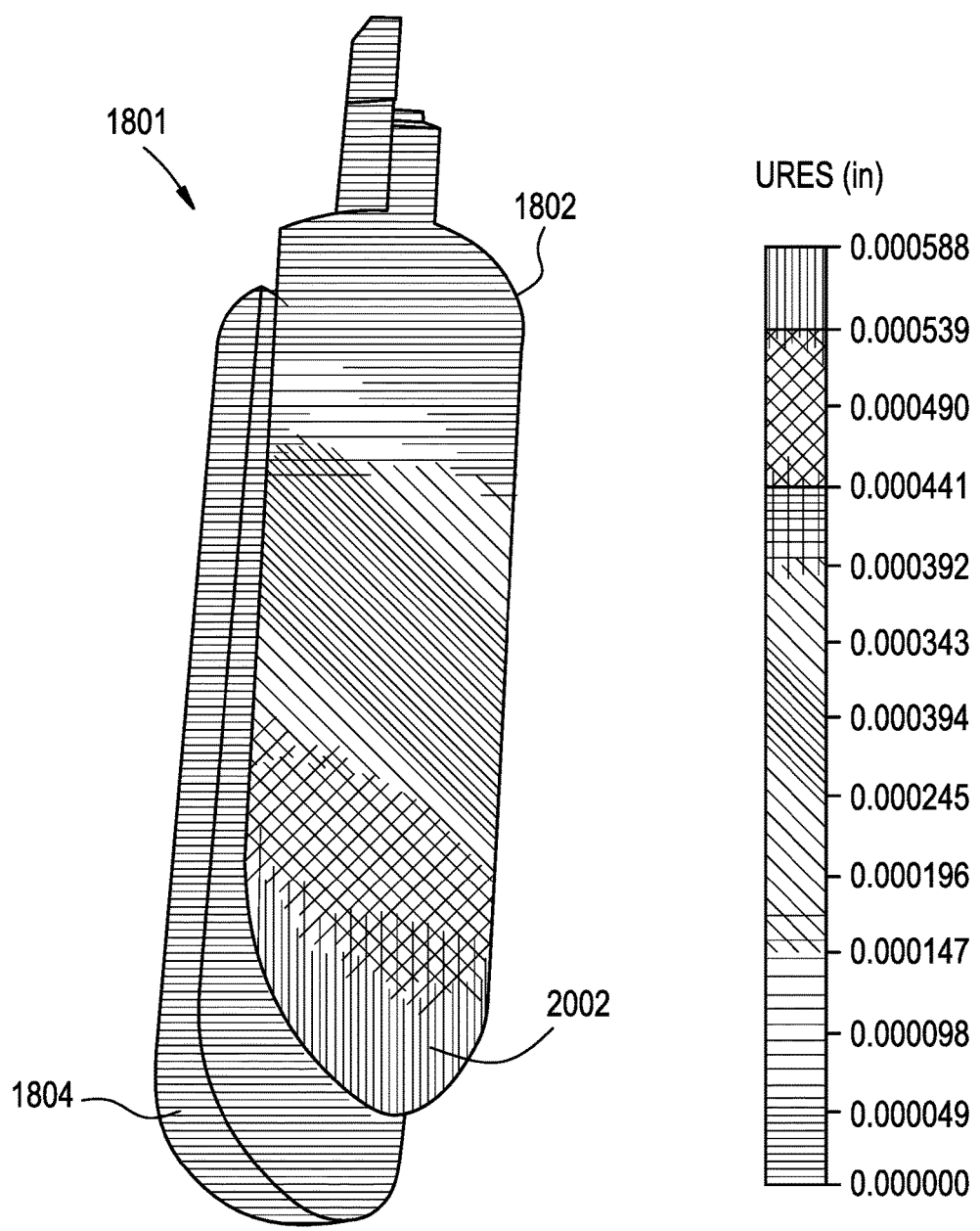
FIG. 20 is an illustration of simulated deflection of the surgical end effector according to the teachings of the present disclosure shown in FIG. 18.

FIGS. 19-22 illustrate simulated finite element analysis results for deflection/displacement and stress in the end effectors 1801 and 1805 in response to about 7 lbf (31.14 newtons) applied to the jaw members in the direction shown by arrows 1810. FIG. 19, for example, indicates that the first jaw member 1806 of the prior art end effector 1805 has a maximum deflection or displacement of about 0.001 inches (0.025 millimeters) at a distal end 1902 thereof, with decreasing levels of deflection moving toward a proximal end thereof. In comparison, the first jaw member 1802 of the end effector 1801 has a maximum deflection or displacement of about 0.0006 inches (0.015 millimeters) at a distal end 2002 thereof, as shown in FIG. 20. The maximum deflection of the end effector 1801, then, is about 40% less than the maximum deflection of the prior art end effector 1805.

Figure 21:
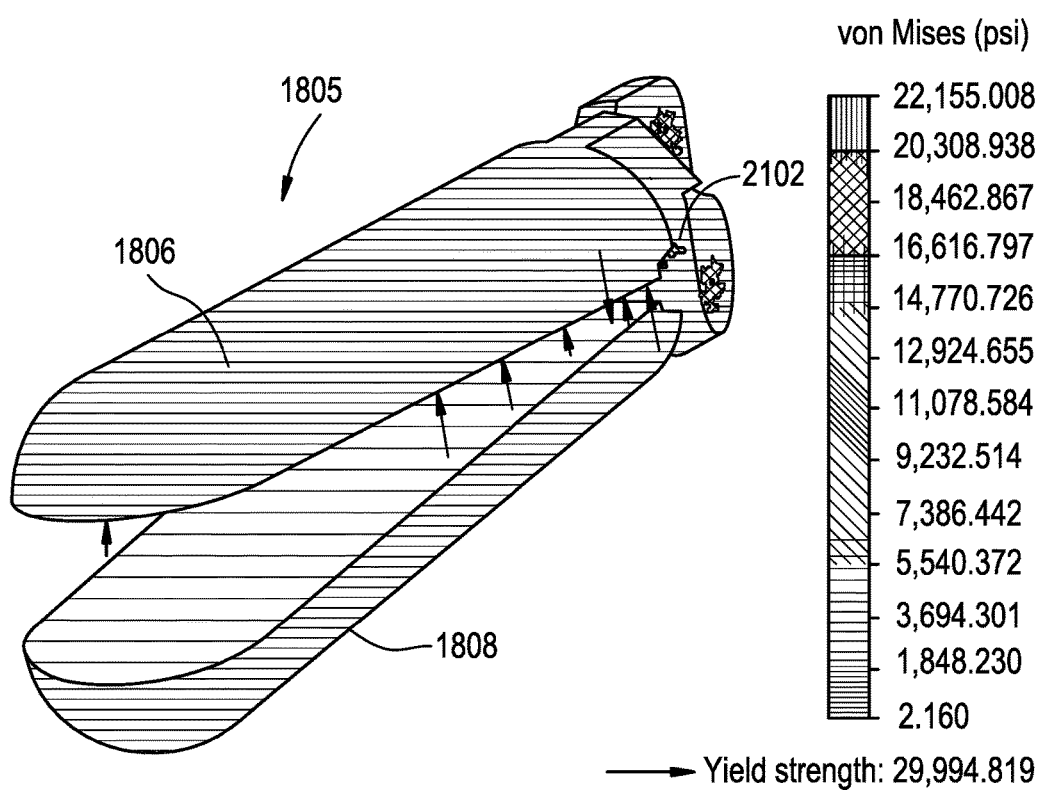
FIG. 21 is an illustration of simulated stress in the prior art surgical instrument shown in FIG. 18.
Figure 22:
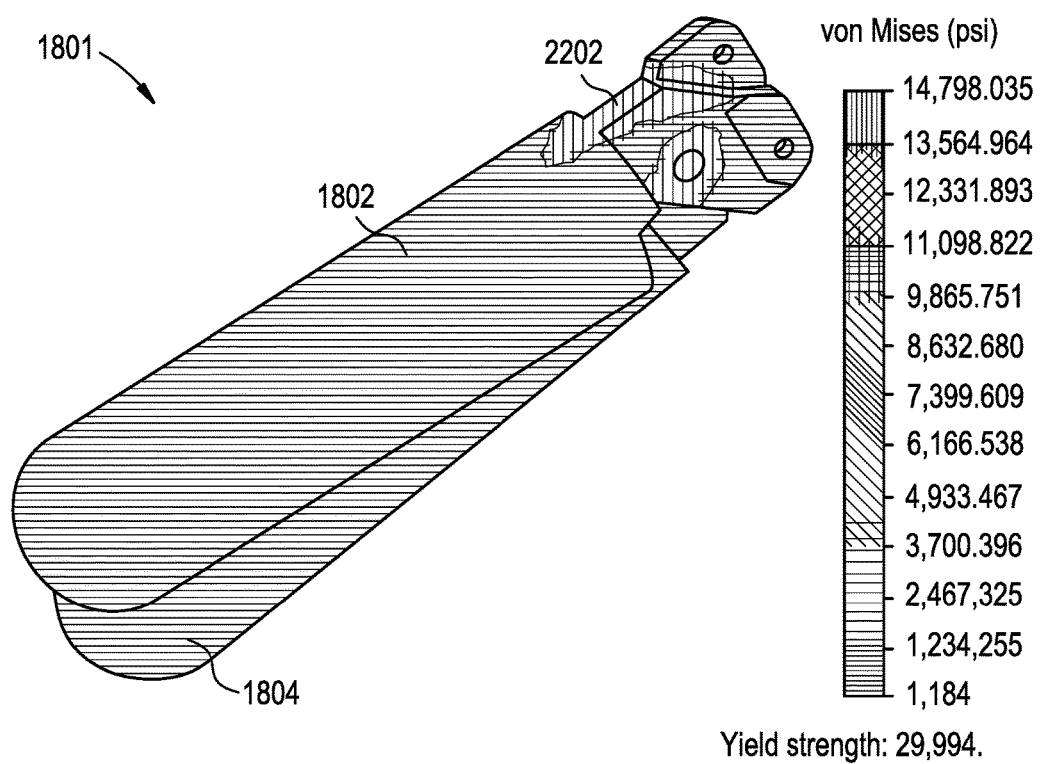
FIG. 22 is an illustration of simulated stress in the surgical end effector according to the teachings of the present disclosure shown in FIG. 18.

FIGS. 21-22 illustrate a similar comparison with regard to measurements of stress within the first jaw member 1802 of the end effector 1801 and the corresponding jaw member 1806 of the prior art end effector 1805. More particularly, FIG. 21 indicates that a maximum stress measurement of about 22.1 ksi ($1.52\times10^8$ N/m$^2$) is found at a proximal end 2102 of the jaw member 1806. In comparison, a maximum stress measurement at a proximal end 2202 of the jaw member 1802 is about 14.7 ksi ($1.01\times10^8$ N/m$^2$). The maximum stress measurement of the end effector 1801, then, is about 34% less than the maximum stress measurement of the prior art end effector 1805.

Figure 23:
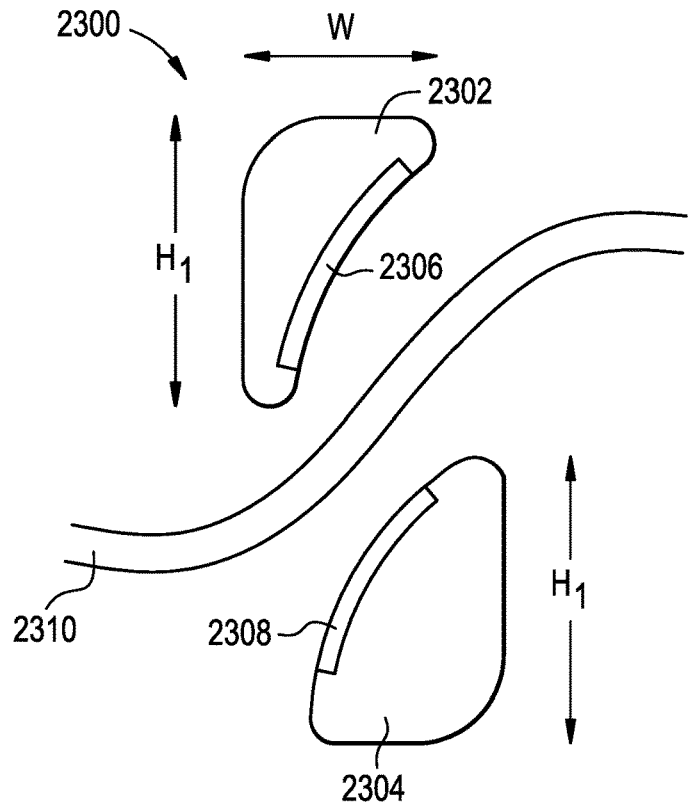
FIG. 23 is a schematic front view illustration of one embodiment of end effector jaw members in an open position.
Figure 24:
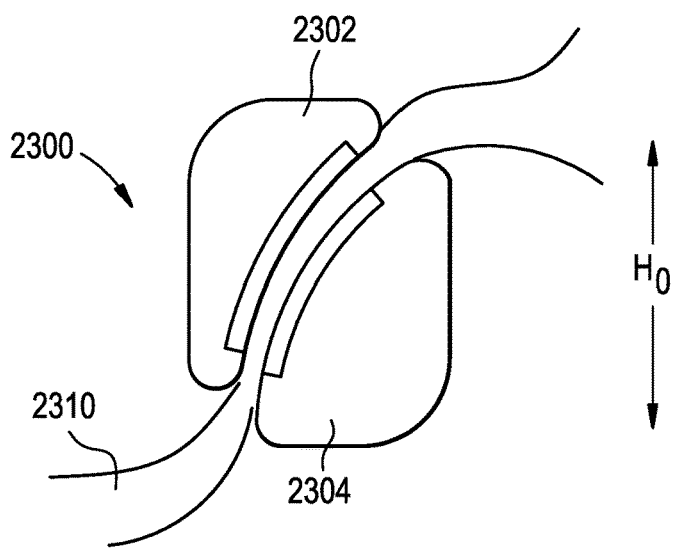
FIG. 24 is a schematic front view illustration of the end effector jaw members of FIG. 23 in a closed position.

FIGS. 23-24 illustrate another embodiment of an end effector 2300 in which jaw member height is increased while minimizing an overall height of the end effector and maximizing a surface area of tissue that is contacted by, for example, an electrode or other energy delivery structure. As shown in the figure, the first jaw member 2302 and the second jaw member 2304 of the end effector 2300 can each have a height $H_1$ that is greater than a width W thereof. In one embodiment, the height $H_1$ can be 4 millimeters, but any other desired dimension is also possible.

In addition to the overall aspect ratio of height relative to width in cross-section, jaw members 2302, 2304 can include complementary tissue-facing surfaces that can each have an electrode or other energy delivery structure 2306, 2308 disposed thereon. The tissue-facing surface of each jaw member can be oriented such that it is transverse to an axis along which width W is measured. In other words, the surface can be transverse to an axis that is perpendicular to a plane in which the first and second jaw members 2302, 2304 pivot or otherwise move relative to one another. In the embodiment illustrated in FIG. 23, for example, the tissue-facing surface of each jaw member 2302, 2304 extends at approximately 45 degrees to the axis along which W is measured. This means that the surface extends between diagonally opposed corners of the end effector when viewing a plane defined by the axes along which height $H_1$ and width W are measured. Orienting the surface in this manner can maximize the surface area that contacts tissue 2310 disposed between the jaw members 2302, 2304 because the tissue-facing surface on each jaw member can have a dimension measured in the plane of the figure that is greater than the overall width W of the end effector 2300.

When the jaw members 2302, 2304 are moved from the open configuration of FIG. 23 to the closed configuration of FIG. 15 to clamp tissue 2310 therebetween, an overall height $H_O$ of the end effector can be minimized. In one embodiment, for example, the overall height $H_O$ can be approximately 5 millimeters, but other overall dimensions are possible based on the sizes of the various jaw members and other components of the surgical instrument. FIG. 24 also illustrates how the tissue 2310 is clamped between the jaw members 2302, 2304 along a tortuous path that follows the shape of the complementary tissue-facing surfaces of the jaw members. As noted above, the length of this tortuous path can be greater than an overall width W of the end effector 2300, thereby providing an increased surface area for passing electrical or other energy through the tissue to create a high quality seal and/or weld.

The tissue-facing surfaces of the jaw members 2302, 2304 can have any of a variety of profiles to maximize surface area that contacts tissue. In some embodiments, for example, the tissue-facing surfaces can be planar, while in other embodiments the surfaces can be curved to provide even greater surface area for contacting tissue. For example, the electrodes 2306, 2308 of FIG. 23, which are disposed on the tissue-facing surfaces of the jaw members 2302, 2304, can have complementary concave/convex shapes to further increase the surface area configured to contact and transmit energy through tissue.

Figure 25:
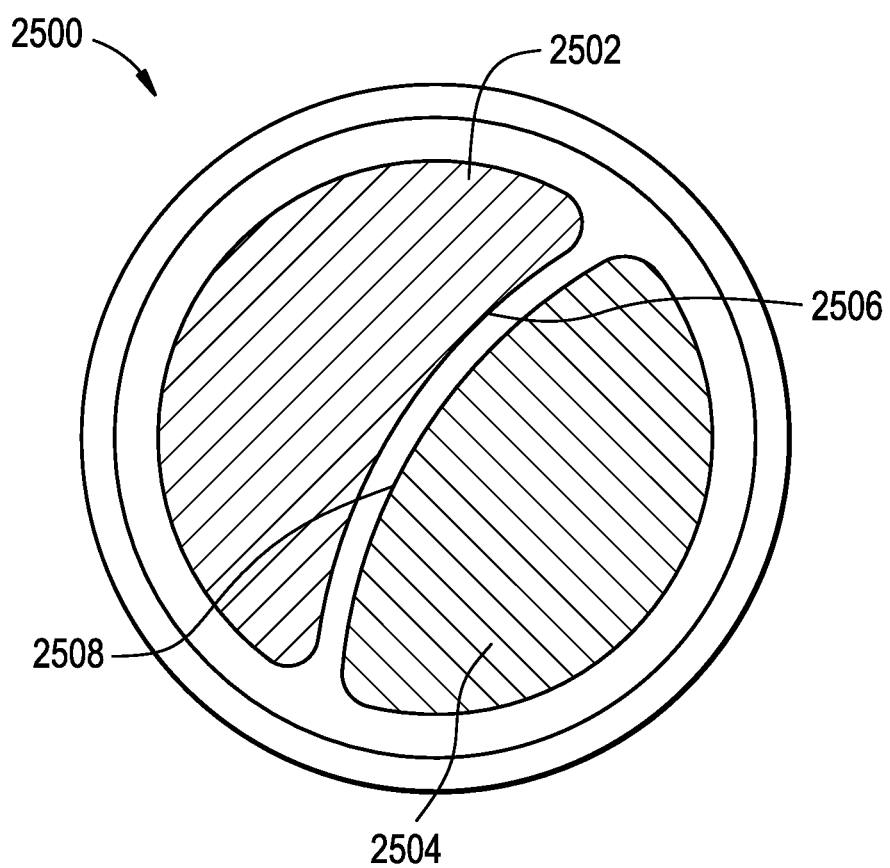
FIG. 25 is a schematic front view illustration of another embodiment of end effector jaw members in a closed position.

FIG. 25 illustrates another embodiment of an end effector 2500 in which a generally cylindrical outer profile is employed along with a curved tortuous path for grasping and sealing tissue. In particular, first jaw member 2502 and second jaw member 2504 can include complementary tissue-facing surfaces 2506, 2508 that include complementary surface curvature. This configuration can increase the surface area of tissue that is contacted when the jaw members are moved to a closed position when compared to planar tissue-facing surfaces.

In still other embodiments, end effectors can be configured to move between a low profile insertion configuration and a larger deployed configuration to allow end effector jaw members with increased height to be used even when insertion through restricted passages is necessary. For example, in the embodiment of FIGS. 26-27, end effector jaw members can be configured to move proximally and distally relative to one another in order to reduce an overall size of the end effector for insertion or removal from a surgical site.

FIG. 26 illustrates a side view of the end effector 2600 in which a first jaw member 2602 and a second jaw member 2604 are arranged in an insertion configuration. In this configuration, a distal end of the first jaw member can be positioned proximal to a distal end of the second jaw member such that the two are not in alignment for clamping tissue, as shown in FIG. 27. In some embodiments, the first jaw member 2602 can be retracted proximally enough that the distal end thereof can be positioned proximal to the proximal end of the second jaw member 2604. Furthermore, in some embodiments the first and second jaw members can be configured to nest with one another to reduce at least one overall dimension (e.g., a height dimension) of the end effector 2600. For example, the nesting arrangement shown in FIG. 26 can allow the overall height $H_O$ of the end effector 2600 to be reduced for insertion through a restricted passageway. In one embodiment, the overall height $H_O$ can be about 5 millimeters, though any other dimension is possible.

Upon arrival at a surgical site, the end effector 2600 can be transitioned from the insertion configuration of FIG. 26 to the deployed configuration of FIG. 27. In this configuration, the first and second jaw members 2602, 2604 can be aligned along the longitudinal axis L. In addition, the end effectors can be positioned such that they no longer nest, and may even be separated from one another, along an axis perpendicular to the longitudinal axis L. As a result, an overall height $H_O$ of the end effector can be larger, e.g., 10 millimeters in one embodiment.

As noted above, end effector widths are often maximized so as to provide the largest surfaces for contacting tissue and transferring electrical or other energy thereto. The larger electrodes and tissue-contacting surface area can create larger areas within the tissue that are sufficiently heated to create a seal and/or weld. Accordingly, reducing end effector width in favor of height could reduce the size of thermal zones created in tissue during a sealing operation. The various embodiments described above involving tortuous pathways, e.g., those shown in FIGS. 13, 17, and 23-25, can increase the electrode surface area contacting tissue and therefore avoid any reduction in thermal zone size.

In other embodiments, however, the delivery of energy from electrodes having a reduced tissue-contacting surface area can be tuned so as to create thermal zones equivalent in size to those created by larger electrodes or other energy delivery structures. For example, electrical or other energy can be delivered over a longer period of time to allow heat generated near the electrode to expand outward therefrom via conduction until a thermal zone of desired size is created in the tissue surrounding the end effector.

FIG. 28 illustrates such an embodiment, in which an end effector 2800 having a height that is greater than a width W thereof uses first and second jaw members 2802, 2804 to grasp one or more layers or bundles of tissue 2806. Electrical or other energy can be delivered through electrodes or other energy delivery structures disposed on, or integrated into, tissue-facing surfaces of the first and second jaw members 2802, 2804. The delivery of energy can be modulated such that a thermal zone is created in the tissue disposed between the jaw members 2802, 2804 and allowed to spread outward therefrom to areas 2808, 2810 adjacent the end effector 2800. If the thermal zone reaches a sufficient temperature, the tissue in these areas can be welded together along with the tissue disposed between the jaw members 2802, 2804. This can yield a tissue seal and/or weld that is equivalent in size to one that can be created with a wider end effector having a larger electrode surface area. Another advantage of such a configuration is that the delivery of energy can be adjusted so as to create different thermal zones in different circumstances. For example, a surgeon or other user might want a smaller thermal zone when operating in the vicinity of a vital organ or other sensitive structure. In other cases, however, a larger thermal zone might be desired to provide higher confidence that a good tissue seal has been created.

The devices disclosed herein can be formed from a variety of materials and can have a variety of different sizes and shapes. For example, the end effectors and other components of surgical instruments described herein can be formed from various polymers and/or metals. Furthermore, particular components can be formed from a different material than other components. By way of further example, a portion of an end effector can be formed from a polymer material, (e.g., polycarbonate), while another portion can be formed from a metal, such as surgical grade stainless steel (e.g., 17-4), other 300 and 400 series stainless steels, titanium, and aluminum, perhaps to take advantage of greater rigidity, electrical conductivity, etc. Of course, these are non-limiting examples of possible material combinations. Device sizes can also vary greatly, depending on the intended use and surgical site anatomy. In particular, devices can be configured to be inserted through passageways of a particular size or diameter, e.g., during introduction to a surgical site through a trocar or other access instrument. Further, a variety of lengths can be employed at any particular diameter to accommodate various end effector sizes, surgical site locations, etc.

The devices disclosed herein can be designed to be disposed of after a single use, or they can be designed to be used multiple times. In either case, however, the device can be reconditioned for reuse after at least one use. Reconditioning can include any combination of the steps of disassembly of the device, followed by cleaning or replacement of particular pieces, and subsequent reassembly. In particular, the device can be disassembled, and any number of the particular pieces or parts of the device can be selectively replaced or removed in any combination. Upon cleaning and/or replacement of particular parts, the device can be reassembled for subsequent use either at a reconditioning facility, or by a surgical team immediately prior to a surgical procedure. Reconditioning a device can utilize a variety of techniques for disassembly, cleaning/replacement, and reassembly. Use of such techniques, and the resulting reconditioned device, are all within the scope of the present application.

The devices described herein can be processed before use in a surgical procedure. First, a new or used instrument can be obtained and, if necessary, cleaned. The instrument can then be sterilized. In one sterilization technique, the instrument can be placed in a closed and sealed container, such as a plastic or TYVEK bag. The container and its contents can then be placed in a field of radiation that can penetrate the container, such as gamma radiation, x-rays, or high-energy electrons. The radiation can kill bacteria on the instrument and in the container. The sterilized instrument can then be stored in the sterile container. The sealed container can keep the instrument sterile until it is opened in the medical facility. Other forms of sterilization known in the art are also possible. This can include beta or other forms of radiation, ethylene oxide, steam, or a liquid bath (e.g., cold soak). Certain forms of sterilization may be better suited to use with different portions of the device due to the materials utilized, the presence of electrical components, etc.

Furthermore, the teachings provided herein can also be applied to surgical methods for use of the above-described devices and/or creation of tissue seals and/or welds. For example, an exemplary method according to the teachings provided herein can include moving opposed jaw members of a surgical instrument end effector from an open position to a closed position to clamp tissue therebetween, applying compressive force to the clamped tissue using a closure mechanism that acts on a proximal end of the jaw members, and delivering energy through the clamped tissue to create a seal and/or weld. Increased stiffness of the opposed jaw members can result in better tissue grasping and improved compression, which can create a better quality tissue seal. In other embodiments, methods might also include inserting a surgical instrument into a patient's body while the jaw members are in an insertion configuration, and moving the end effector jaw members to a deployed configuration before clamping tissue. Still other variations are possible based on the teachings provided herein, all of which are considered within the scope of the present application.

One skilled in the art will appreciate further features and advantages of the disclosure based on the above-described embodiments. Accordingly, the disclosure is not to be limited by what has been particularly shown and described, except as indicated by the appended claims. All publications and references cited herein are expressly incorporated herein by reference in their entirety.

What is claimed is:

1. A surgical end effector, comprising:
   first and second jaw members movable relative to one another between an open position and a closed position to clamp tissue therebetween;
   wherein the first and second jaw members each have a height measured at a proximal end thereof that is greater than half of an overall height of the end effector with the jaw members in the closed position;
   wherein a sum of heights of the first and second jaw members measured at a distal end thereof is approximately equal to the overall height of the end effector with the jaw members in the closed position;
   wherein height is measured along an axis that is perpendicular to a longitudinal axis of the end effector and contained within a plane in which the first and second jaw members move relative to one another; and
   wherein the first jaw member has a first tissue contacting surface and the second jaw member has a second tissue-contacting surface that opposes the first tissue contacting surface such that the first and second tissue-contacting surfaces substantially overlap with each other in the plane in which the first and second tissue-contacting surfaces tapers linearly so the height of the first jaw member and the height of the second jaw member each decrease in a distal direction.

2. The end effector of claim 1, further comprising an actuator coupled to at least one of the first and second jaw members and configured to move it relative to the other jaw member.

3. The end effector of claim 2, wherein the actuator is pivotably coupled to the at least one of the first and second jaw members and configured to translate along the longitudinal axis of the end effector.

4. The end effector of claim 3, wherein the actuator is further configured to contact the at least one of the first and second jaw members with a planar distal-facing surface when the first and second jaw members are in the closed position.

5. The end effector of claim 1, wherein each tissue-contacting surface is configured to abut against tissue clamped between the first and second jaw members when in the closed position, and wherein an electrode is disposed on the tissue-contacting surface of at least one of the first and second jaw members.

6. The end effector of claim 5, wherein at least one of the first and second jaw members includes sidewalls that extend from the tissue contacting surface such that tissue is stretched between the sidewalls as the first and second jaw members move from the open position to the closed position.

7. The end effector of claim 1, wherein each of the first and second jaw members includes a slot formed along a length thereof that is configured to receive a cutting element configured to cut tissue clamped between the first and second jaw members.

8. The end effector of claim 7, wherein the slots are formed in the first and second tissue-contacting surfaces.

9. A surgical end effector, comprising:
   a first jaw member having sidewalls defining a central recess with a first tissue-contacting surface, wherein a height of the sidewalls increases from a distal end to a proximal end of the first jaw member;
   a second jaw member pivotably coupled to the first jaw member and including a central portion with a second tissue-contacting surface, the central portion being configured to be received within the central recess of the first jaw member, wherein a height of the central portion increases from a distal end to a proximal end of the second jaw member; and
   wherein a slot extends substantially along a length of both of the first and second tissue-contacting surfaces such that distal translation of a cutting element through the slot causes the first and second jaw members to move from an open position to a closed position.

10. The end effector of claim 9, wherein the height of the sidewalls of the first jaw member at the proximal end thereof and the height of the central portion of the second jaw member at the proximal end thereof are each greater than half of an overall height of the end effector at a proximal end thereof with the first and second jaw members in a closed position.

11. The end effector of claim 9, wherein the height of the sidewalls of the first jaw member and the height of the central portion of the second jaw member increase linearly from the distal end thereof to the proximal end thereof.

12. The end effector of claim 9, further comprising an electrode disposed on the tissue-contacting surface of at least one of the first and second jaw members, the electrode being configured to contact tissue clamped between the first and second jaw members.

13. A surgical end effector, comprising:
   first and second jaw members movable relative to one another between a low profile configuration, in which a distal end of the first jaw member is in a first position proximal to a distal end of the second jaw member, and a higher profile configuration, in which the distal end of the first jaw member is in a second position distal to the first position; and
   an electrode disposed on a surface of at least one of the first and second jaw members, the electrode being configured to contact tissue clamped between the first and second jaw members;
   wherein a height of each of the first and second jaw members is greater than a width thereof, the height being measured along a first axis that is perpendicular to a longitudinal axis of the end effector and contained within a plane in which the first and second jaw members move relative to one another, the width being measured along a second axis that is perpendicular to both the longitudinal axis of the end effector and the first axis;
   wherein the distal ends of the first and second jaw members are aligned with each other along the first axis when the jaw members are in the higher profile configuration, and
   wherein the end effector has a first overall height when the jaw members are in the low profile configuration, and the end effector has a second overall height when the jaw members are in the higher profile configuration, the second overall height being greater than the first overall height.

14. The end effector of claim 13, wherein the surface is planar.

15. The end effector of claim 13, wherein the surface is curved.

16. The end effector of claim 13, wherein the surface extends between diagonally opposed corners of the end effector when viewing a plane defined by the first axis and the second axis.

17. The end effector of claim 13, wherein the first jaw member includes the surface and the second jaw member includes a complementary surface facing the surface.

18. The end effector of claim 17, wherein the complementary surface of the second jaw member also includes an electrode disposed thereon.

19. The end effector of claim 13, wherein each of the first and second jaw members includes a slot formed along a length thereof that is configured to receive a cutting element configured to cut tissue clamped between the first and second jaw members.

* * * * *